United States Patent
Chun et al.

(10) Patent No.: US 9,681,932 B2
(45) Date of Patent: Jun. 20, 2017

(54) INTRAORAL BIOFILM CONTROL APPARATUS

(71) Applicant: Hankookin, Inc., Raleigh, NC (US)

(72) Inventors: James Jiwen Chun, Raleigh, NC (US); Andrew Youngho Chun, Raleigh, NC (US); Angela Soyoung Chun, Raleigh, NC (US); Jennifer Miseong Chun, Raleigh, NC (US)

(73) Assignee: HANKOOKIN, INC., Raleigh, NC (US)

( * ) Notice: Subject to any disclaimer, the term of this patent is extended or adjusted under 35 U.S.C. 154(b) by 156 days.

(21) Appl. No.: 14/261,828

(22) Filed: Apr. 25, 2014

(65) Prior Publication Data

US 2014/0322668 A1    Oct. 30, 2014

Related U.S. Application Data

(60) Provisional application No. 61/815,872, filed on Apr. 25, 2013.

(51) Int. Cl.
*A61C 17/06* (2006.01)

(52) U.S. Cl.
CPC .................. *A61C 17/043* (2013.01)

(58) Field of Classification Search
CPC ............................ A61C 17/043; A61C 17/046
USPC ................................ 433/91, 92, 93, 95, 96
See application file for complete search history.

(56) References Cited

U.S. PATENT DOCUMENTS

| | | | | |
|---|---|---|---|---|
| 4,799,885 A | * | 1/1989 | Hussong | A61C 17/04 137/38 |
| 4,806,101 A | * | 2/1989 | Rossi | A61C 17/04 433/91 |
| 5,114,415 A | * | 5/1992 | Shedlock | A61M 1/008 604/319 |
| 5,176,654 A | * | 1/1993 | Schreiber | A61F 11/00 604/181 |
| 5,390,663 A | * | 2/1995 | Schaefer | A61B 1/227 600/200 |
| 5,876,384 A | * | 3/1999 | Dragan | A61M 1/008 433/91 |
| 6,217,328 B1 | * | 4/2001 | Oliver | A61C 1/0084 433/29 |

(Continued)

*Primary Examiner* — Nicholas Lucchesi
(74) *Attorney, Agent, or Firm* — Ash Tankha; Lipton, Weinberger & Husick

(57) ABSTRACT

An intraoral biofilm control apparatus including a suction unit, a suction chamber positioned within and in communication with an inner space of the suction unit, a tubular connection member operably connected to and extending into the suction chamber, and an angular head member adjustably connected to an upper end of the tubular connection member is provided. The suction chamber, in communication with the suction unit, creates a negative air pressure in an inner space of the suction chamber. The angular head member in fluid communication with the suction chamber via the tubular connection member, contacts and suctions the intraoral biofilm from the intraoral areas into the inner space of the suction chamber when the negative air pressure is created. The angular head member having an angularly curved suction tip configurably accesses the intraoral areas. The angular head member having a suction plate suctions the intraoral biofilm from intraoral tongue areas.

9 Claims, 22 Drawing Sheets

(56) References Cited

U.S. PATENT DOCUMENTS

| | | | | |
|---|---|---|---|---|
| 6,406,484 B1* | 6/2002 | Lang | ............ | A61M 1/0023 |
| | | | | 604/35 |
| 6,602,071 B1* | 8/2003 | Ellion | ............ | A46B 11/063 |
| | | | | 132/322 |
| 8,474,467 B2* | 7/2013 | Coates | ............ | A61C 15/00 |
| | | | | 132/321 |
| 2006/0219813 A1* | 10/2006 | Morrison | ............ | B05B 1/3442 |
| | | | | 239/334 |
| 2008/0154183 A1* | 6/2008 | Baker | ............ | A61M 1/0058 |
| | | | | 604/28 |
| 2009/0281482 A1* | 11/2009 | Baker | ............ | A61M 1/0058 |
| | | | | 604/28 |
| 2009/0281483 A1* | 11/2009 | Baker | ............ | A61M 1/0058 |
| | | | | 604/28 |
| 2012/0059224 A1* | 3/2012 | Wellen | ............ | A61B 1/2275 |
| | | | | 600/200 |
| 2013/0178808 A1* | 7/2013 | Chen | ............ | A61M 1/0023 |
| | | | | 604/319 |

\* cited by examiner

INTRAORAL BIOFILM CONTROL APPARATUS

CROSS REFERENCE TO RELATED APPLICATIONS

This application claims priority to and the benefit of provisional patent application No. 61/815,872 titled "Intraoral Biofilm Control Apparatus", filed in the United States Patent and Trademark Office on Apr. 25, 2013. The specification of the above referenced patent application is incorporated herein by reference in its entirety.

BACKGROUND

Plaque is a form of an intraoral biofilm that forms on and around teeth and that attaches to intraoral areas, for example, oral enamel, gingival surfaces, gingival tissues, teeth, restorations, etc. The intraoral biofilm is a complex community of microorganisms that attaches to intraoral areas, for example, the teeth, gums, etc. An initial layer of plaque formed in the intraoral areas is referred to as an acquired pellicle. The acquired pellicle reforms within about two hours after removal of the acquired pellicle from the intraoral areas. The acquired pellicle also forms on artificial prostheses, for example, braces, dental partials, etc. With over 700 species of aerobic and anaerobic bacteria residing in the human oral cavity, microbes grow as complex colonies in the form of an intraoral biofilm also referred in literature as plaque. Within about two days, if not removed from the oral cavity, the plaque approximately doubles in mass. If the plaque is not removed from the intraoral areas in the oral cavity, the plaque may mineralize and become calculus, aided by calcium and phosphates present in saliva. Plaque contributes to oral diseases such as dental caries and periodontal disease. Furthermore, published literature has shown a correlation between dental health and the overall health and longevity of a person.

Conventional methods used for oral care such as brushing, flossing, tongue scraping, etc., disrupt the plaque but do not completely remove the plaque from the intraoral areas. Intraoral rinsing or rinsing of the oral cavity removes portions of the disrupted plaque that are dissolved in the rinsing solution, but does not remove the plaque that adheres to teeth, gingival surfaces, and inaccessible intraoral areas in between the teeth and in between the villi on the surface of the tongue, leading to reformation of the plaque. Persons using oral prostheses such as braces, bridges, dental partials, etc., have larger surface areas in their oral cavities on which the plaque is retained after brushing, flossing, tongue scraping, rinsing, etc.

Failure to timely remove the plaque from the intraoral areas in the oral cavity may result in dental and/or oral diseases comprising, for example, halitosis generically referred to as bad breath, destruction of tooth enamel, tooth decay, tooth root and gum infections, etc. Moreover, if the plaque buildup continues, these dental and/or oral diseases may result in permanent damage to gums causing breakdown of the bone supporting a tooth. Furthermore, swallowing the bacteria present in the plaque increases the probability of an infection spreading to other parts of the body, including the upper respiratory system and the upper digestive system.

Hence, there is a long felt but unresolved need for an intraoral biofilm control apparatus that controls deposition and mineralization of an intraoral biofilm by timely removal of the intraoral biofilm from accessible and inaccessible intraoral areas using negative air pressure. Furthermore, there is a need for a method that employs the intraoral biofilm control apparatus for suctioning the intraoral biofilm from intraoral areas by creating a negative air pressure in the intraoral biofilm control apparatus.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

The intraoral biofilm control apparatus disclosed herein addresses the above stated needs for controlling deposition and mineralization of an intraoral biofilm, also referred to as plaque, by timely removal of the intraoral biofilm from accessible and inaccessible intraoral areas using negative air pressure. The intraoral biofilm control apparatus disclosed herein comprises a suction unit, a suction chamber, a tubular connection member, and an angular head member. The suction unit is configured as a flexible container defining an inner space. The suction chamber is positioned within and in communication with the inner space of the suction unit. The suction chamber, in communication with the suction unit, creates a negative air pressure in an inner space defined within the suction chamber for suctioning an intraoral biofilm from intraoral areas into the inner space of the suction chamber. The suction chamber receives the suctioned intraoral biofilm. The tubular connection member is operably connected to the suction unit. The tubular connection member extends into the suction chamber positioned within the suction unit. The tubular connection member is in fluid communication with the inner space of the suction chamber.

The angular head member is adjustably connected to an upper end of the tubular connection member. In an embodiment, the angular head member comprises a generally curved body having an upper end and a lower end. The lower end of the generally curved body of the angular head member is adjustably connected to the suction unit via the tubular connection member. The angular head member contacts the intraoral biofilm in the intraoral areas. The angular head member, in fluid communication with the inner space of the suction chamber in the suction unit via the tubular connection member, suctions the intraoral biofilm from the intraoral areas into the inner space of the suction chamber when a negative air pressure is created in the inner space of the suction chamber. In an embodiment, the angular head member comprises a suction tip positioned on the upper end of the generally curved body of the angular head member for accessing and contacting intraoral areas. The suction tip is angularly curved to reach inaccessible intraoral areas. In an embodiment, the suction tip is removably connected to the upper end of the angular head member for enabling replacement of the suction tip. The suction tip, in communication with the suction unit via the tubular connection member, suctions the intraoral biofilm from the intraoral areas when a negative air pressure is created in the suction unit. In an embodiment, the angular head member is rotatably connected to the tubular connection member to enable the suction tip to configurably access the intraoral areas and contact the intraoral biofilm in the intraoral areas.

In another embodiment, the angular head member comprises a generally circular suction plate removably connected to the upper end of the tubular connection member. The circular suction plate, in fluid communication with the inner space of the suction chamber in the suction unit via the tubular connection member, suctions the intraoral biofilm from intraoral tongue areas into the inner space of the suction chamber when a negative air pressure is created in the inner space of the suction chamber. In another embodiment, the angular head member comprises a micro brush tip positioned on the upper end of the generally curved body of the angular head member. The micro brush tip is configured to remove the intraoral biofilm from readily accessible intraoral areas.

In an embodiment, the suction unit of the intraoral biofilm control apparatus comprises the suction chamber and one or more air line tubes inserted into the suction chamber. When the suction unit is decompressed and a negative air pressure is created in the inner space of the suction chamber, the air line tubes allow air and any intraoral biofilm to be suctioned through the angular head member into the inner space of the suction chamber.

In an embodiment, the suction unit comprises the suction chamber and compressible members of a generally elliptical shape. The compressible members are operably connected on opposing sides of the suction chamber via air line tubes in the suction unit. The compressible members are in fluid communication with the inner space of the suction chamber via the air line tubes. When the compressible members are decompressed and a negative air pressure is created in an inner space defined within each of the compressible members and the inner space of the suction chamber, the compressible members allow air and any intraoral biofilm to be suctioned through the angular head member into the inner space of the suction chamber. In another embodiment, the suction unit comprises the suction chamber and a suction pump. The suction pump is operably connected to the suction chamber via an air line tube in the suction unit. The suction pump creates a negative air pressure in the inner space of the suction chamber for suctioning the intraoral biofilm from the intraoral areas through the angular head member and via the tubular connection member into the inner space of the suction chamber. In an embodiment, a negative air pressure is created using an external decompressing suction unit, for example, a dental suction line connected to a vacuum source used in a dental office.

Also, disclosed herein is a method that employs the intraoral biofilm control apparatus for suctioning an intraoral biofilm from intraoral areas by creating a negative air pressure in the intraoral biofilm control apparatus. The intraoral biofilm control apparatus comprising the suction unit, the suction chamber positioned within and in communication with the inner space of the suction unit, the tubular connection member, and the angular head member as disclosed above is provided. The intraoral biofilm control apparatus is inserted into an oral cavity of the patient. The angular head member of the inserted intraoral biofilm control apparatus is positioned at an intraoral area to contact the intraoral biofilm in the intraoral area. A negative air pressure is created in the inner space of the suction chamber of the inserted intraoral biofilm control apparatus by compressing and decompressing the suction unit of the inserted intraoral biofilm control apparatus. When the negative air pressure is created in the inner space of the suction chamber, the positioned angular head member, in fluid communication with the inner space of the suction chamber in the suction unit via the tubular connection member, suctions the intraoral biofilm from the intraoral area into the inner space of the suction chamber.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing carries over to the description of that method step or structure shown by that same numeral in any subsequent drawing herein.

DETAILED DESCRIPTION OF THE INVENTION

Figure 1A:
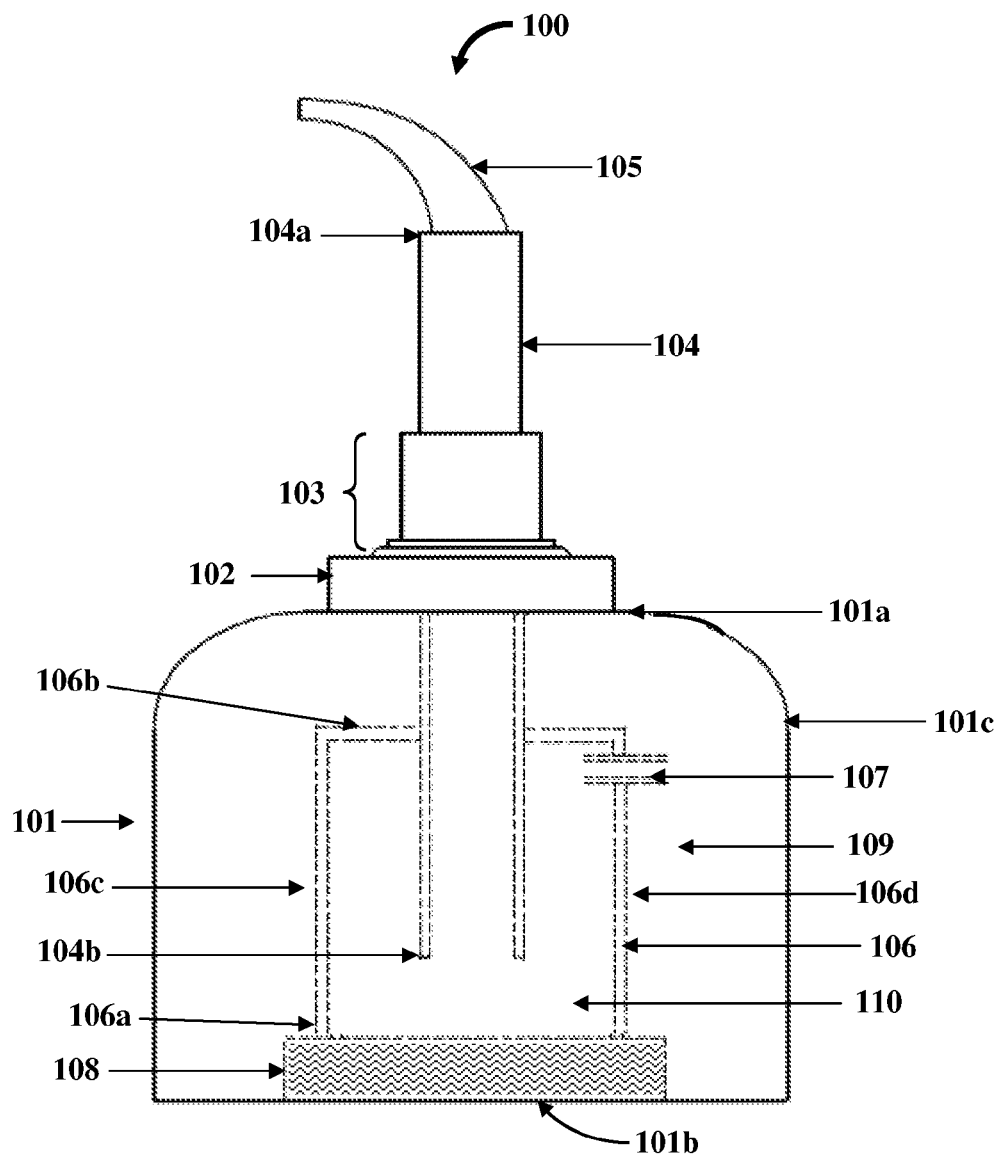
FIG. 1A exemplarily illustrates a front elevation view of an intraoral biofilm control apparatus, showing a suction unit of the intraoral biofilm control apparatus.

FIG. 1A exemplarily illustrates a front elevation view of an intraoral biofilm control apparatus 100, showing a suction unit 101 of the intraoral biofilm control apparatus 100. As used herein, "intraoral biofilm" refers to a grouping of microorganisms that attaches to intraoral areas, for example, oral enamel, gingival surfaces, gingival tissues, teeth, restorations, etc., and causes one or more oral diseases. Also, as used herein, "intraoral areas" refer to regions within an oral cavity, that is, structures comprising, for example, the teeth, the tongue, the palate, a base of the oral cavity, an oral vestibule, etc., to which an intraoral biofilm can attach. The intraoral biofilm control apparatus 100 is used for suctioning the intraoral biofilm from the intraoral areas using negative air pressure, for example, an air pressure that is below the standard atmospheric pressure of 1 atmosphere or about 14.7 pounds per square inch absolute (psia). As used herein, "negative air pressure" refers to a state of vacuum created in a closed chamber. The intraoral biofilm control apparatus 100 disclosed herein is used for oral care and for maintaining oral hygiene in different users, for example, infant users, adult users, animal users, etc., by controlling and removing intraoral biofilm from their oral cavities. The intraoral biofilm control apparatus 100 disclosed herein employs a suction mechanism using a negative air pressure for removal and control of the intraoral biofilm from the intraoral areas for oral care. After intraoral biofilm layers are disrupted by methods comprising, for example, brushing, flossing, tongue scraping, etc., the intraoral biofilm control apparatus 100 disclosed herein can be used to remove the remaining intraoral biofilm through suction.

As exemplarily illustrated in FIG. 1A, the intraoral biofilm control apparatus 100 disclosed herein comprises a suction unit 101, a suction chamber 106, a tubular connection member 104, and an angular head member 105. The suction unit 101 is made of a compressible material, for example, polyethylene. In an embodiment, the suction unit 101 is configured as a flexible bottle shaped container with a generally cylindrical wall 101c, an upper surface 101a, and a generally circular lower surface 101b, as exemplarily illustrated in FIGS. 1A-1B. The cylindrical wall 101c, the upper surface 101a, and the circular lower surface 101b of the suction unit 101 define an inner space 109 in the suction unit 101. The suction unit 101 can be compressed by manually exerting a moderate amount of pressure, for example, with a user's hand, on the cylindrical wall 101c of the suction unit 101. When the exerted compressive pressure or hand force is removed from the cylindrical wall 101c of the suction unit 101, the suction unit 101 retracts to an original decompressed configuration of the suction unit 101.

A generally annular sealing member 102 is rigidly attached on an upper surface 101a of the suction unit 101. An intermediate connection member 103 extends upwardly from the annular sealing member 102. The intermediate connection member 103 rigidly connects to the tubular connection member 104. In an embodiment, the annular sealing member 102 is removably attached to the upper surface 101a of the suction unit 101. The tubular connection member 104 is rigidly connected to the suction unit 101 via the intermediate connection member 103 and the annular sealing member 102. The angular head member 105 is adjustably connected to an upper end 104a of the tubular connection member 104. In an embodiment, the angular head member 105 is removably connected to the upper end 104a of the tubular connection member 104. As exemplarily illustrated in FIGS. 1A-1B, in an embodiment, the angular head member 105 is angularly curved to reach inaccessible intraoral areas. The angular head member 105 is positioned by a user, for example, a dentist in an oral cavity of a patient to contact the intraoral biofilm in the intraoral areas. In an embodiment, the angular head member 105 can be removed and replaced with an angular head member 105 of another shape or size to allow the angular head member 105 to access and contact different intraoral areas, for example, areas in between the teeth, areas under the tongue, gum areas, etc.

The suction chamber 106 of the intraoral biofilm control apparatus 100 is positioned within and in communication with the inner space 109 of the suction unit 101. The suction chamber 106, in communication with the suction unit 101, creates a negative air pressure in an inner space 110 defined within the suction chamber 106 for suctioning and receiving the intraoral biofilm from the intraoral areas into the inner space 110 of the suction chamber 106. The tubular connection member 104 is operably connected to the suction unit 101 and extends into the suction chamber 106 positioned within the suction unit 101. The tubular connection member 104 is in fluid communication with the inner space 110 of the suction chamber 106. The angular head member 105, in fluid communication with the inner space 110 of the suction chamber 106 in the suction unit 101 via the tubular connection member 104, suctions the intraoral biofilm from the intraoral areas into the inner space 110 of the suction chamber 106 when a negative air pressure is created in the inner space 110 of the suction chamber 106.

The intraoral biofilm control apparatus 100 further comprises an air line tube 107 inserted into the suction chamber 106 positioned within the suction unit 101, to facilitate fluid communication between the inner space 110 of the suction chamber 106 and the inner space 109 of the suction unit 101. The air line tube 107 extends outwardly from the suction chamber 106 into the inner space 109 of the suction unit 101. In an embodiment, the intraoral biofilm control apparatus 100 further comprises more than one air line tube 107 inserted into the suction chamber 106 and positioned on opposing sides 106c and 106d of the suction chamber 106. The air line tube 107 is positioned proximal to an upper end 106b of the suction chamber 106 to preclude suctioning of the suctioned intraoral biofilm into the inner space 109 of the suction unit 101 from the inner space 110 of the suction chamber 106. The air line tube 107 is positioned substantially above a lower end 104b of the tubular connection member 104 for precluding the suctioned intraoral biofilm that flows through the tubular connection member 104, from entering the air line tube 107, when the suction unit 101 is decompressed and a negative air pressure is created in the inner space 110 of the suction chamber 106. The air line tube 107 allows air and the intraoral biofilm from the intraoral areas to be suctioned through the angular head member 105 into the inner space 110 of the suction chamber 106 when the suction unit 101 is decompressed and a negative air pressure is created in the inner space 110 of the suction chamber 106.

The intraoral biofilm control apparatus 100 further comprises an airtight sealing member 108 operably connected to a lower end 106a of the suction chamber 106. The airtight sealing member 108 is configured as an end cap for allowing a user, for example, a dentist to open the lower end 106a of the suction chamber 106 to drain the suctioned and accumulated intraoral biofilm from the suction chamber 106. In an embodiment, the airtight sealing member 108 is removably connected to the lower end 106a of the suction chamber 106. In another embodiment, the airtight sealing member 108 is hingedly connected to the lower end 106a of the suction chamber 106.

Figure 1B:
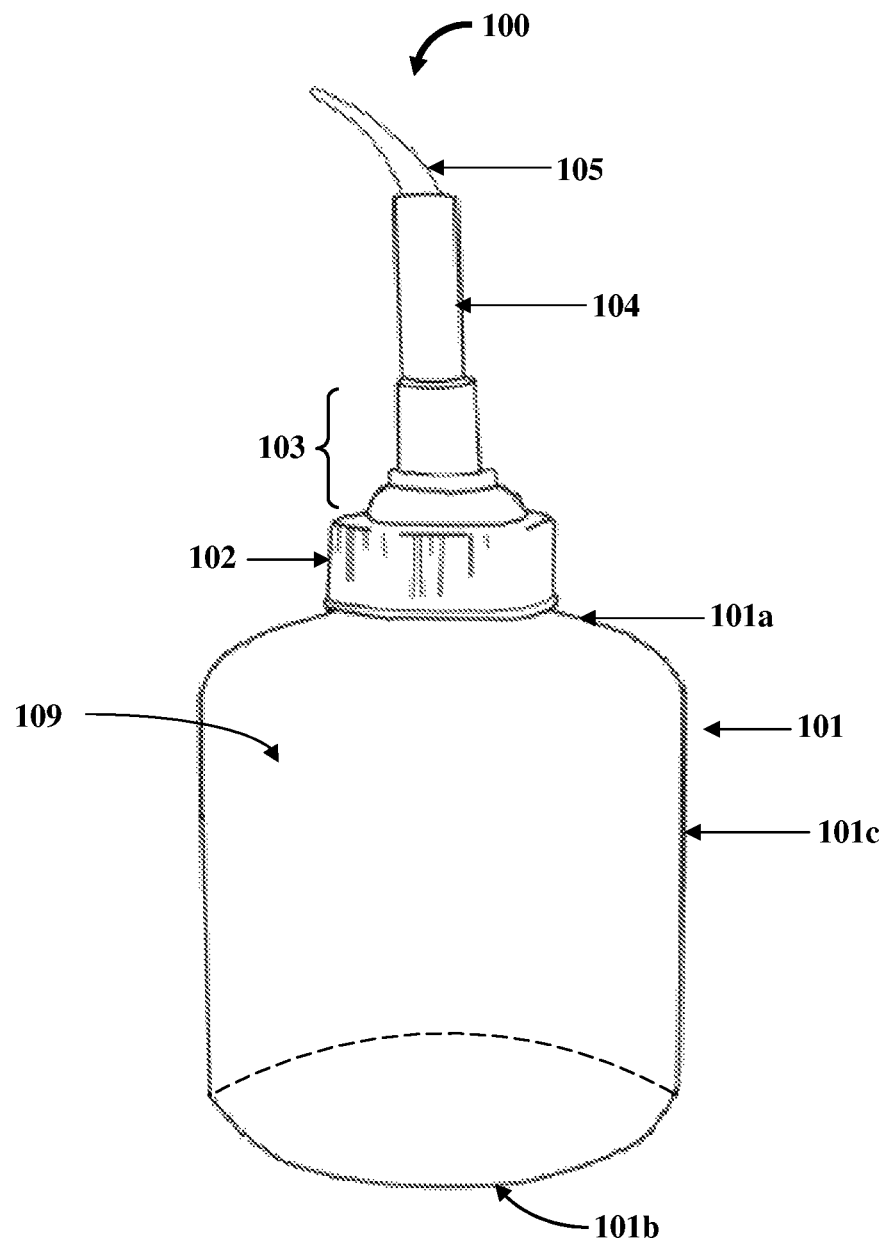
FIG. 1B exemplarily illustrates a front perspective view of the intraoral biofilm control apparatus.

FIG. 1B exemplarily illustrates a front perspective view of the intraoral biofilm control apparatus 100. The intraoral biofilm control apparatus 100 comprises the suction unit 101, the annular sealing member 102, the intermediate connection member 103, the tubular connection member 104, and the angular head member 105 as disclosed in the detailed description of FIG. 1A. Not shown in FIG. 1B, in dashed lines, is the suction chamber 106, the air line tube 107, and the airtight sealing member 108 positioned inside the suction unit 101 as exemplarily illustrated in FIG. 1A. As exemplarily illustrated in FIG. 1B, the suction unit 101 is configured as a compressible bottle shaped container with a generally cylindrical wall 101c, an upper surface 101a, and a generally circular lower surface 101b that define the inner space 109 of the suction unit 101. The compressible bottle shaped container is compressed and decompressed to create a negative air pressure inside the suction chamber 106 positioned inside the suction unit 101, for suctioning the intraoral biofilm in contact with the angular head member 105 through the tubular connection member 104 and into the suction chamber 106 as disclosed in the detailed description of FIG. 1A.

Figure 2:
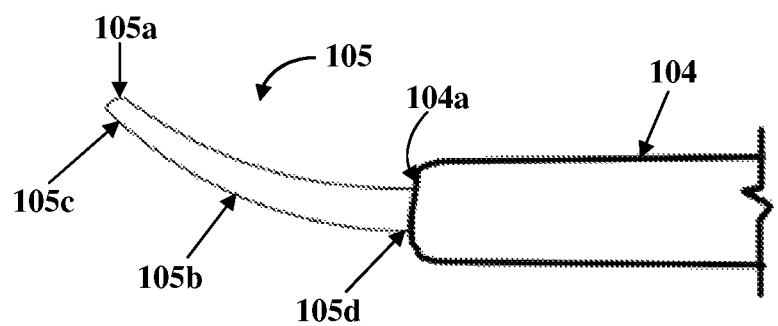
FIG. 2 exemplarily illustrates an enlarged view of an embodiment of the angular head member of the intraoral biofilm control apparatus.

FIG. 2 exemplarily illustrates an enlarged view of an embodiment of the angular head member 105 of the intraoral biofilm control apparatus 100 exemplarily illustrated in FIGS. 1A-1B. In this embodiment, the angular head member 105 comprises a generally curved body 105b having an upper end 105c and a lower end 105d. In an embodiment, the angular head member 105 further comprises a suction tip 105a positioned on the upper end 105c of the curved body 105b for accessing and contacting intraoral areas. In an embodiment, the suction tip 105a is removably connected to the upper end 105c of the curved body 105b for enabling replacement of the suction tip 105a. In this embodiment, the suction tip 105a can be removed and replaced to maintain hygiene when the intraoral biofilm control apparatus 100 is repeatedly used from one patient to another. The suction tip 105a accesses accessible and inaccessible intraoral areas in an oral cavity. As exemplarily illustrated in FIG. 2, the suction tip 105a is angularly curved to reach inaccessible intraoral areas. The lower end 105d of the curved body 105b of the angular head member 105 is adjustably connected to the upper end 104a of the tubular connection member 104 of the intraoral biofilm control apparatus 100. The angular head member 105 can therefore be connected to the suction unit 101 of the intraoral biofilm control apparatus 100 via the tubular connection member 104. In this embodiment, the suction tip 105a, in communication with the suction unit 101 via the tubular connection member 104, suctions the intraoral biofilm from the intraoral areas into the suction chamber 106 exemplarily illustrated in FIG. 1A, when a negative pressure is created in the suction chamber 106 within the suction unit 101. The curved body 105b of the angular head member 105 is configured as a hollow tubular body for transferring the intraoral biofilm from the intraoral areas via the suction tip 105a to the suction chamber 106 positioned inside the suction unit 101 via the tubular connection member 104.

Figure 3A:
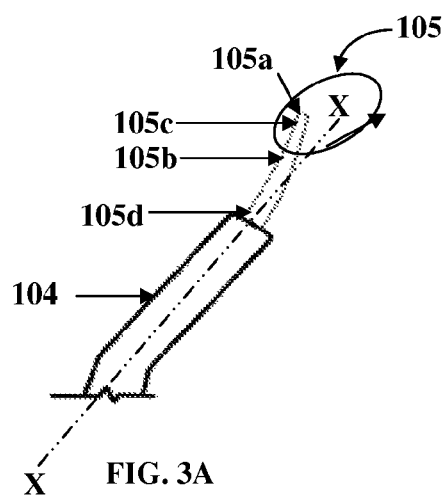
FIGS. 3A-3C exemplarily illustrate enlarged views of an embodiment of the angular head member of the intraoral biofilm control apparatus.
Figure 3B:
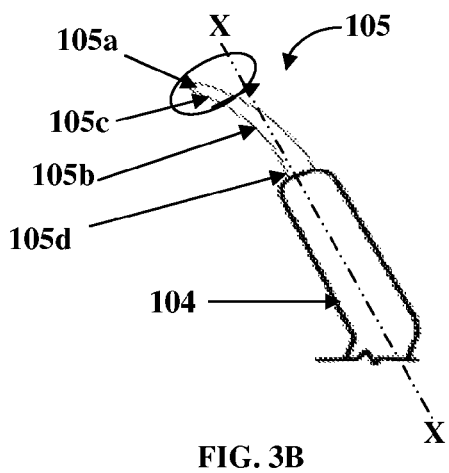
Figure 3C:
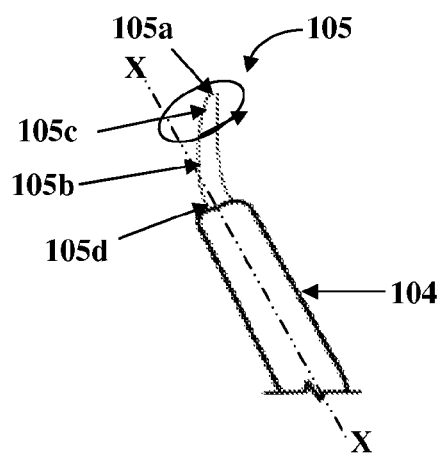

FIGS. 3A-3C exemplarily illustrate enlarged views of an embodiment of the angular head member 105 of the intraoral biofilm control apparatus 100 exemplarily illustrated in FIGS. 1A-1B. In this embodiment, the angular head member 105 is rotatably connected to the tubular connection member 104 to enable the suction tip 105a to configurably access the intraoral areas and contact the intraoral biofilm in the intraoral areas. The angular head member 105 with the suction tip 105a rotates or swivels around a vertical axis XX passing through the tubular connection member 104, to allow a user, for example, a dentist to configurably access and reach intraoral areas in a patient's oral cavity for suctioning the intraoral biofilm from the intraoral areas via the suction tip 105a. The suction tip 105a of the angular head member 105 is angularly curved to reach inaccessible intraoral areas, for example, in between the teeth, between braces, between a dental under bridge, deep inside the oral cavity, etc., for suctioning the intraoral biofilm from the intraoral areas. The suction tip 105a is of predetermined dimensions comprising, for example, a predetermined length, a predetermined diameter, a predetermined width, etc., and can be easily maneuvered within the intraoral areas. The suction tip 105a can be configured, for example, as a dental scaler tip used by a dental hygienist to remove plaque and calculus between teeth. For patients with braces, the suction tip 105a can reach under inaccessible intraoral areas and remove the intraoral biofilm that is located in inaccessible intraoral areas, for example, in between the braces.

Figure 4A:
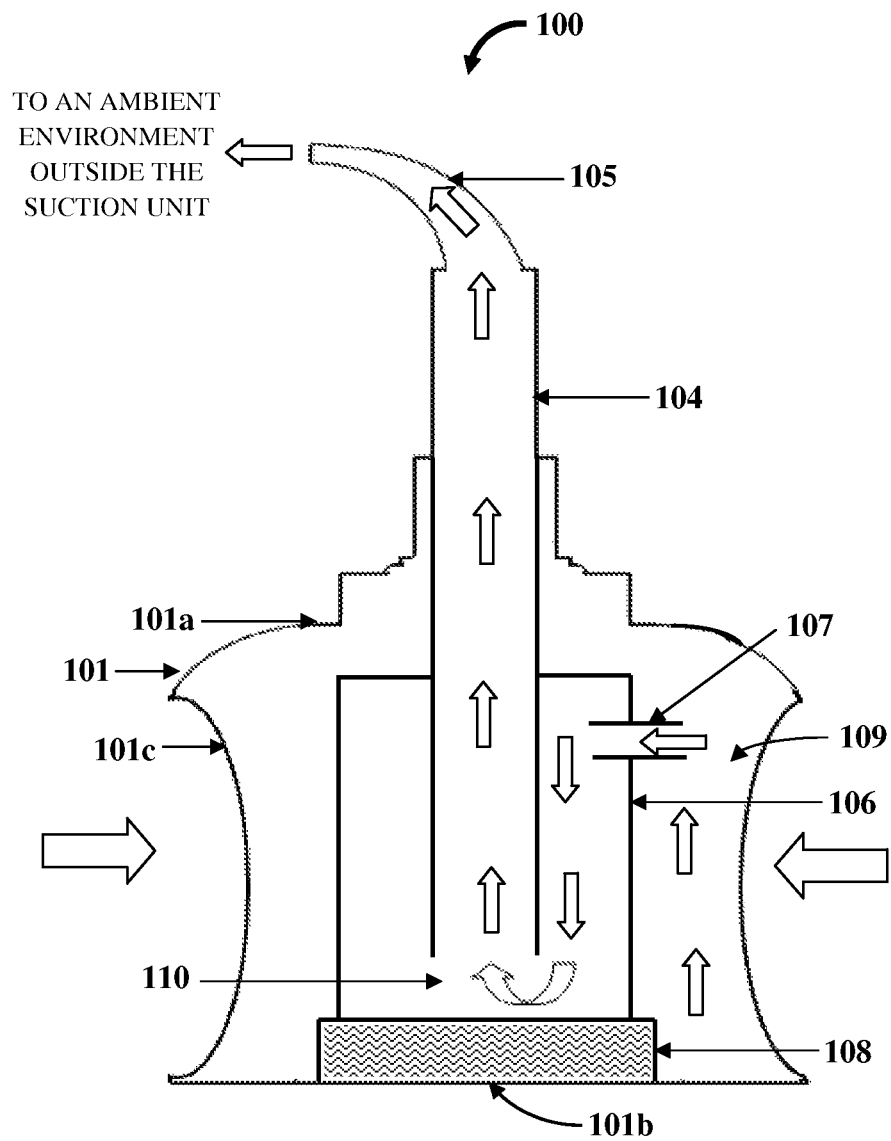
FIGS. 4A-4B exemplarily illustrate sectional views of the intraoral biofilm control apparatus, showing a suction unit when compressed and decompressed respectively.
Figure 4B:
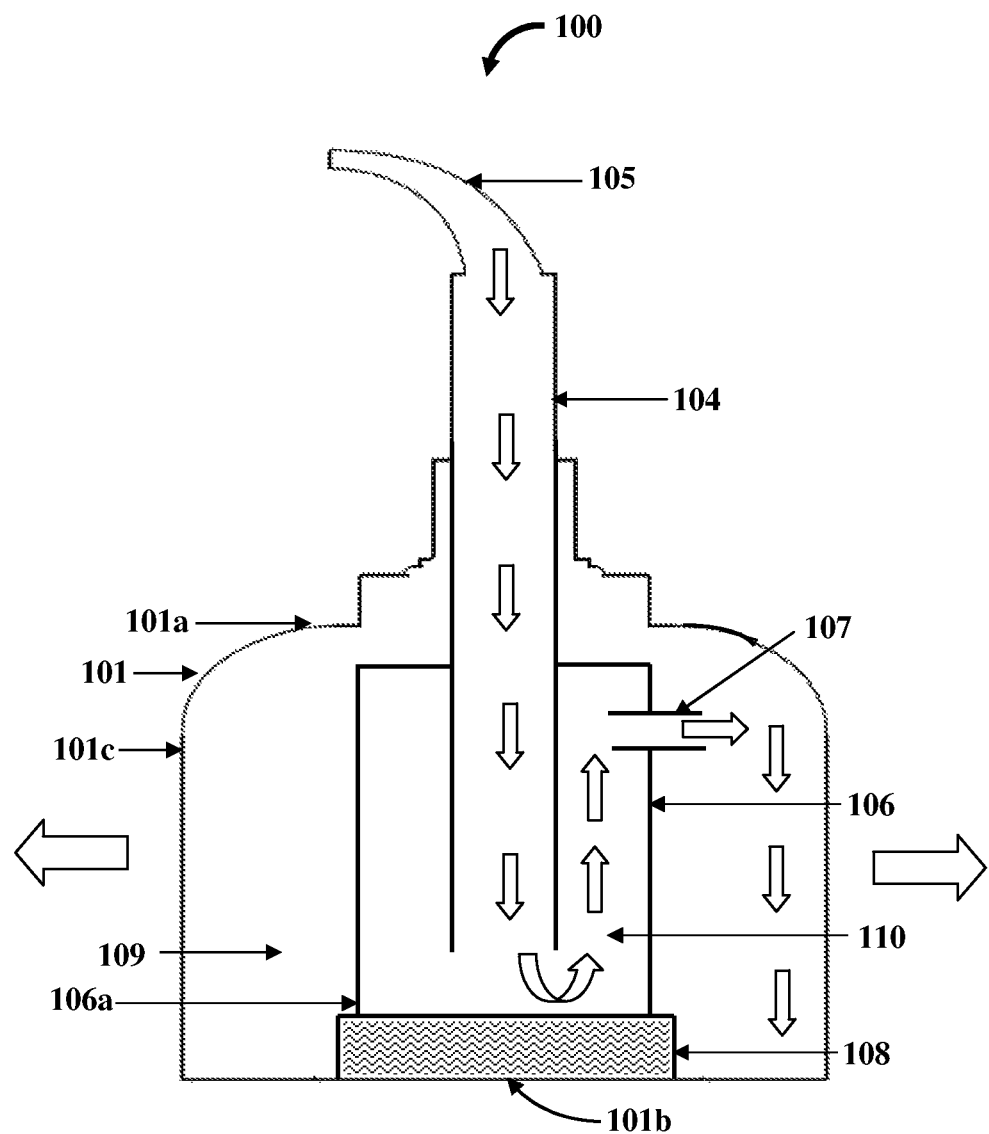

FIGS. 4A-4B exemplarily illustrate sectional views of the intraoral biofilm control apparatus 100, showing a suction unit 101 when compressed and decompressed respectively. In an embodiment, the suction unit 101 is configured as a compressible bottle shaped container with a generally cylindrical wall 101c, an upper surface 101a, and a generally circular lower surface 101b. The suction unit 101 comprises the suction chamber 106 with the airtight sealing member 108 and the air line tube 107 as disclosed in the detailed description of FIG. 1A. On manually compressing the suction unit 101, for example, with a user's hand, at the cylindrical wall 101c of the suction unit 101 as exemplarily illustrated in FIG. 4A, air from the inner space 109 of the suction unit 101 is exhausted out of the suction unit 101 through the angular head member 105 of the intraoral biofilm control apparatus 100 via the air line tube 107, the suction chamber 106, and the tubular connection member 104 as exemplarily illustrated by arrows indicating air flow in FIG. 4A. The air from the inner space 109 of the suction unit 101 passes through the air line tube 107, into the tubular connection member 104, and out through the angular head member 105. After compressing the suction unit 101, when the compressive pressure exerted on the cylindrical wall 101c of the suction unit 101 is released, the suction unit 101 retracts to an original decompressed configuration of the suction unit 101 creating a negative air pressure in the inner space 110 of the suction chamber 106. Due to this negative air pressure created in the inner space 110 of the suction chamber 106, the suction unit 101 suctions air from within the inner space 110 of the suction chamber 106 through the air line tube 107 and into the inner space 109 of the suction unit 101 as exemplarily illustrated by arrows indicating air flow in FIG. 4B, to retract to the original decompressed configuration of the suction unit 101. Due to the decompression of the suction unit 101, the intraoral biofilm is suctioned from the intraoral areas through the angular head member 105 into the tubular connection member 104 and thereafter into the inner space 110 of the suction chamber 106. A user, for example, a dentist can open the lower end 106a of the suction chamber 106 by opening the airtight sealing member 108 to drain the intraoral biofilm accumulated in the suction chamber 106. If the angular head member 105 is blocked, for example, by an obstacle, the suction unit 101 can be compressed to remove the obstacles in the angular head member 105. By manually compressing the suction unit 101, for example, with a user's hand, at the cylindrical wall 101c, air forces the obstacle out of the suction tip 105a of the angular head member 105 into an ambient environment outside the suction unit 101 as exemplarily illustrated in FIG. 4A.

Figure 5A:
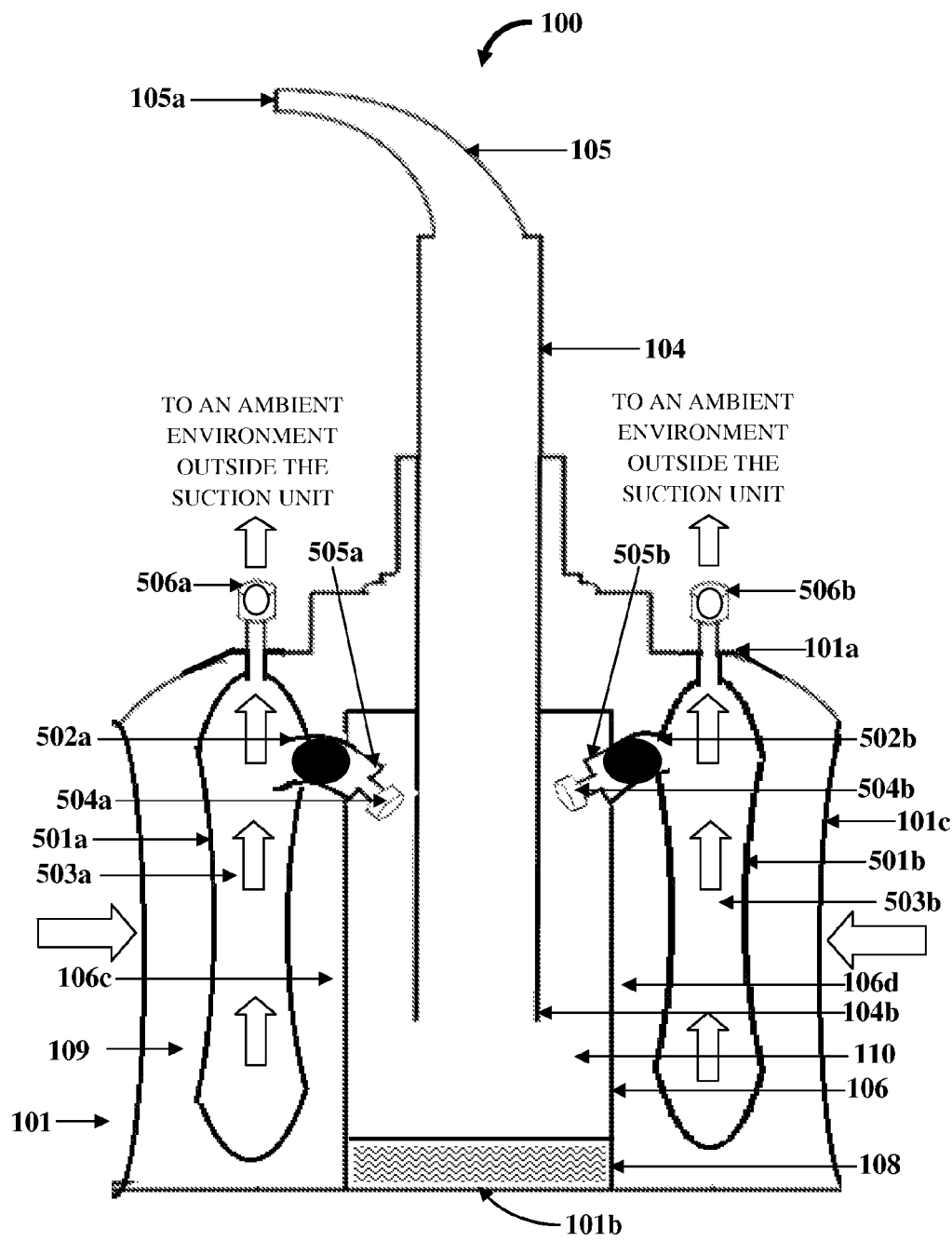
FIGS. 5A-5B exemplarily illustrate sectional views of an embodiment of the intraoral biofilm control apparatus, showing a suction unit when compressed and decompressed respectively.
Figure 5B:
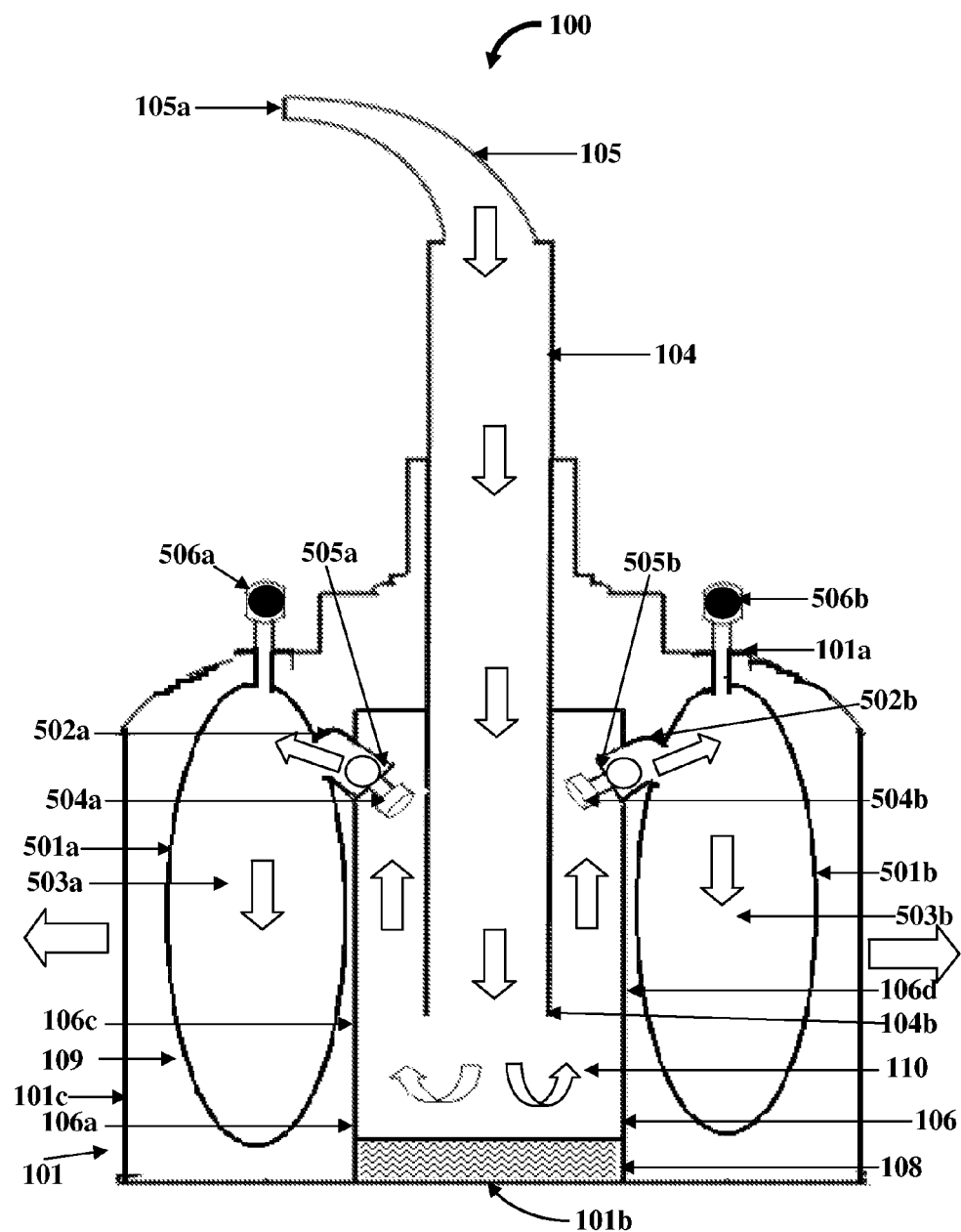

FIGS. 5A-5B exemplarily illustrate sectional views of an embodiment of the intraoral biofilm control apparatus 100, showing a suction unit 101 when compressed and decompressed respectively. In this embodiment, in addition to the suction chamber 106 with the airtight sealing member 108, the suction unit 101 further comprises compressible members 501a and 501b of a generally elliptical shape that allow a continuous air pumping action, thereby creating a continuous negative pressure in the suction chamber 106 positioned within the suction unit 101. In this embodiment, the suction unit 101 is configured as a compressible bottle shaped container with a generally cylindrical wall 101c, an upper surface 101a, and a generally circular lower surface 101b defining an inner space 109 of the suction unit 101 as exemplarily illustrated in FIG. 5A. The suction unit 101 is made of a compressible material, for example, polyethylene. In this embodiment, the compressible members 501a and 501b are configured as air bags. The compressible members 501a and 501b are operably connected on opposing sides 106c and 106d of the suction chamber 106 via the air line tubes 502a and 502b in the suction unit 101. The compressible members 501a and 501b are in fluid communication with the inner space 110 of the suction chamber 106 via the air line tubes 502a and 502b. The air line tubes 502a and 502b are positioned substantially above the lower end 104b of the tubular connection member 104 for precluding the suctioned intraoral biofilm that flows through the tubular connection member 104, from entering the air line tubes 502a and 502b, when the suction unit 101 is decompressed and a negative air pressure is created in the inner space 110 of the suction chamber 106.

As exemplarily illustrated in FIG. 5A, when the suction unit 101 is manually compressed by exerting a moderate amount of pressure, for example, by a user's hand, on the cylindrical wall 101c of the suction unit 101, the compressible members 501a and 501b are also compressed. The compressed compressible members 501a and 501b exhaust the air out from inner spaces 503a and 503b defined within the compressible members 501a and 501b respectively, into an ambient environment outside the suction unit 101, for example, via outflow valves 506a and 506b respectively. The direction of air flow during compression is exemplarily illustrated by arrows in FIG. 5A. In an embodiment, the suction unit 101 compresses the compressible members 501a and 501b to exhaust air out through the air line tubes 502a and 502b into the inner space 110 of the suction chamber 106 and out through the suction tip 105a of the angular head member 105 via the tubular connection member 104, if inflow valves 504a and 504b of the intraoral biofilm control apparatus 100, are configured in a way to allow air flow from the inner spaces 503a and 503b of the compressible members 501a and 501b respectively, into the inner space 110 of the suction chamber 106 via the air line tubes 502a and 502b respectively.

After manually compressing the suction unit 101, the compressive pressure exerted on the cylindrical wall 101c of the suction unit 101 is released. On releasing the compressive pressure, the suction unit 101 and, in turn, the compressible members 501a and 501b retract to an original decompressed configuration of the suction unit 101 and the compressible members 501a and 501b respectively, as exemplarily illustrated in FIG. 5B. The decompressed compressible members 501a and 501b create a negative air pressure in each of the inner spaces 503a and 503b of the compressible members 501a and 501b respectively, and in the inner space 110 of the suction chamber 106, and suction air and any intraoral biofilm from the angular head member 105 into the inner space 110 of the suction chamber 106 via the tubular connection member 104. The direction of air flow during decompression is exemplarily illustrated by arrows in FIG. 5B. The suctioned intraoral biofilm is accumulated in the suction chamber 106. A user, for example, a dentist can open the lower end 106a of the suction chamber 106 by opening the airtight sealing member 108 to drain the intraoral biofilm accumulated in the suction chamber 106. The compression and decompression of the compressible members 501a and 501b creates an air pressure drop below a standard atmosphere pressure (atm), for example, about 0.99 atm to about 0.2 atm in the inner space 110 of the suction chamber 106. The suction chamber 106 suctions air and any associated intraoral biofilm from the intraoral areas through the angular head member 105 into the inner space 110 of the suction chamber 106 as exemplarily illustrated in FIG. 5B.

In an embodiment, the intraoral biofilm control apparatus 100 further comprises outflow valves 506a and 506b and the inflow valves 504a and 504b. The inflow valves 504a and 504b are operably connected to the distal ends 505a and 505b of the air line tubes 502a and 502b respectively. The inflow valves 504a and 504b, when opened, allow a unidirectional flow of air from the inner space 110 of the suction chamber 106 into the inner spaces 503a and 503b of the compressible members 501a and 501b via the air line tubes 502a and 502b respectively. The distal ends 505a and 505b of the air line tubes 502a and 502b respectively, are in fluid communication with the inner space 110 of the suction chamber 106. The outflow valves 506a and 506b are operably connected to the compressible members 501a and 501b respectively. The outflow valves 506a and 506b, when opened, allow a unidirectional flow of air from the inner spaces 503a and 503b of the compressible members 501a and 501b respectively to the ambient environment outside the suction unit 101 as exemplarily illustrated in FIG. 5A, for enabling a continuous air pumping action to create a continuous negative air pressure in each of the inner spaces 503a and 503b of the compressible members 501a and 501b respectively and in the inner space 110 of the suction chamber 106. When the compressible members 501a and 501b are compressed, the inflow valves 504a and 504b close and the outflow valves 506a and 506b open to allow air from the inner spaces 503a and 503b of the compressible members 501a and 501b respectively to flow to the ambient environment outside the suction unit 101 as exemplarily illustrated in FIG. 5A.

When the suction unit 101 and the compressible members 501a and 501b are decompressed, the inflow valves 504a and 504b open and the outflow valves 506a and 506b close, thereby allowing air suctioned at the angular head member 105 to be exhausted into the inner spaces 503a and 503b of the compressible members 501a and 501b via the open inflow valves 504a and 504b respectively as exemplarily illustrated in FIG. 5B. During decompression, the inflow valves 504a and 504b open and draw air from the inner space 110 of the suction chamber 106 into the inner spaces 503a and 503b of the compressible members 501a and 501b respectively through the air line tubes 502a and 502b. This suctioned air increases the volume of air inside each of the compressible members 501a and 501b to a volume of air that was originally present inside each of the compressible members 501a and 501b before compression of the compressible members 501a and 501b. The closed outflow valves 506a and 506b preclude air flow from the inner spaces 503a and 503b of the compressible members 501a and 501b respectively to the ambient environment outside the suction unit 101 to enable retraction of the compressible members 501a and 501b to an original decompressed configuration.

Thus, when the suction unit 101 is compressed and when the outflow valves 506a and 506b open, the outflow valves 506a and 506b allow a unidirectional air flow from within the inner spaces 503a and 503b of the compressible members 501a and 501b respectively to the ambient environment outside the suction unit 101. When the suction unit 101 is decompressed, a negative air pressure is created in each of the inner spaces 503a and 503b of the compressible members 501a and 501b respectively and in the inner space 110 of the suction chamber 106 as a result of the air that was exhausted via the open outflow valves 506a and 506b during compression. This negative air pressure created inside the inner space 110 of the suction chamber 106 during decompression of each of the compressible members 501a and 501b and the open inflow valves 504a and 504b respectively, allows a unidirectional, continuous air flow from the suction tip 105a of the angular head member 105 into each of the compressible members 501a and 501b via the air line tubes 502a and 502b respectively, thereby facilitating suctioning of the intraoral biofilm received at the suction tip 105a of the angular head member 105 into the inner space 110 of the suction chamber 106. Thus, the compression and decompression of the suction unit 101 and each of the compressible members 501a and 501b in communication with the outflow valves 506a and 506b and the inflow valves 504a and 504b respectively, allow a continuous air pumping action and therefore a continuous creation of negative air pressure in the suction chamber 106.

If the suction tip 105a of the angular head member 105 is blocked, for example, by an obstacle and if the inflow valves 504a and 504b are positioned in a way to allow air flow from each of the compressible members 501a and 501b into the suction chamber 106, then the compressible members 501a and 501b can be compressed to remove the obstacle by exhausting air from the inner spaces 503a and 503b of the compressible members 501a and 501b respectively, out of the suction tip 105a of the angular head member 105, via the air line tubes 502a and 502b respectively, or the angular head member 105 can be replaced. That is, the unidirectional air flows provided by the inflow valves 504a and 504b allow the blocked suction tip 105a of the angular head member 105 to be either replaced or to be cleared and unblocked based on the air flow direction allowed by the inflow valves 504a and 504b.

Figure 6A:
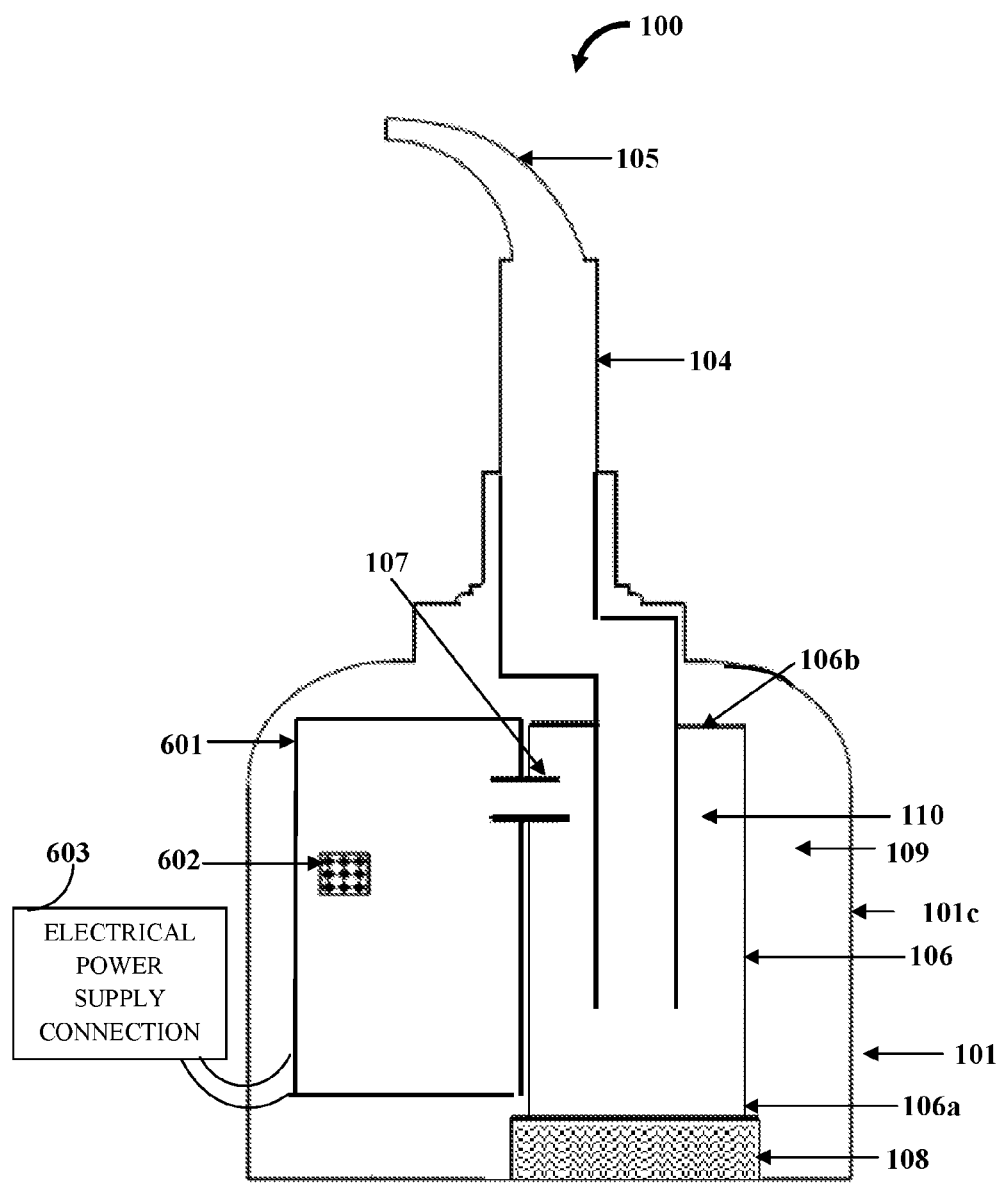
FIG. 6 exemplarily illustrates a sectional view of another embodiment of the intraoral biofilm control apparatus, showing a suction pump for facilitating a continuous air pumping action.
Figure 6B:
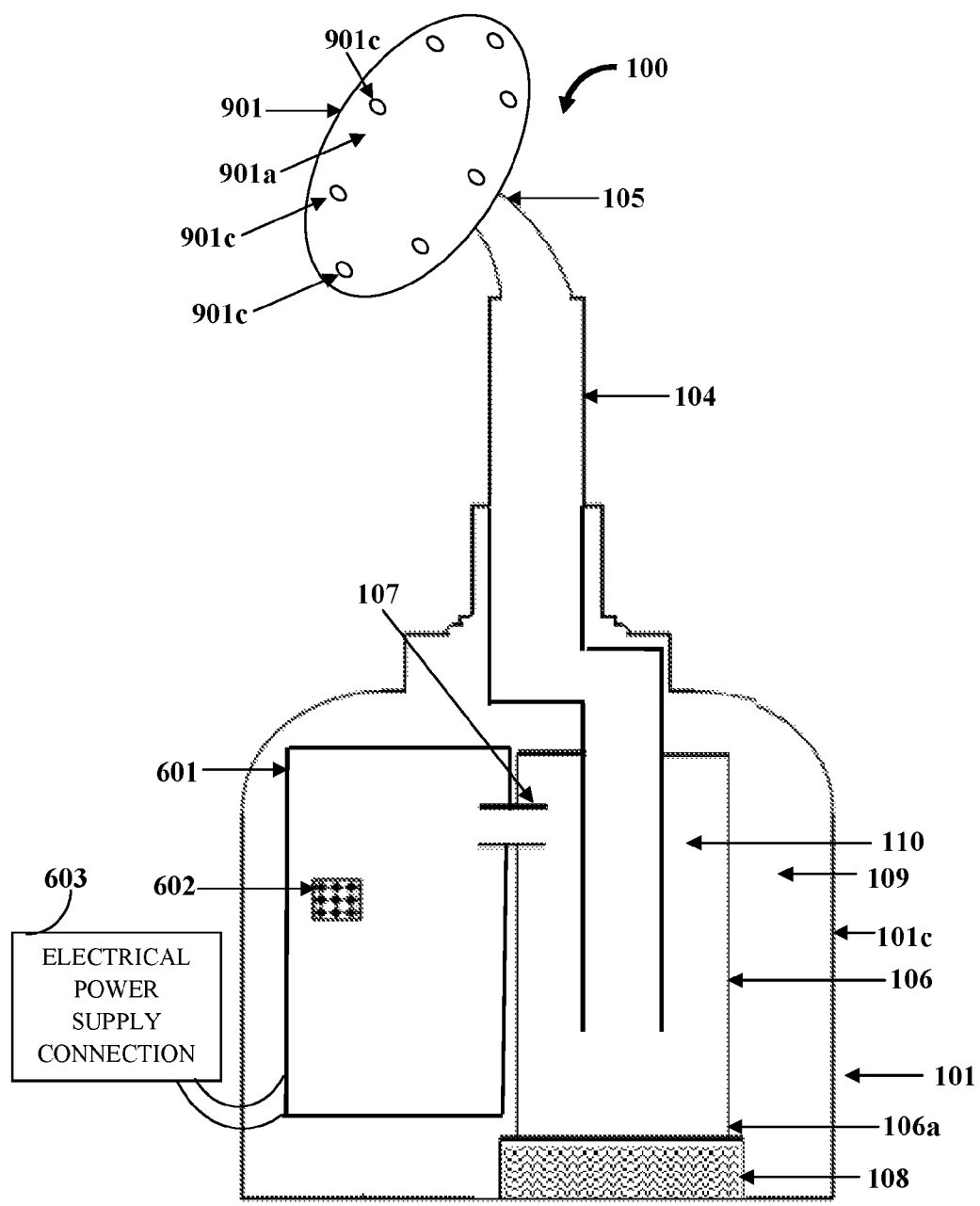

FIGS. 6A and 6B exemplarily illustrate sectional views of another embodiment of the intraoral biofilm control apparatus 100, showing a suction pump 601 for facilitating a continuous air pumping action. In this embodiment, in addition to the suction chamber 106 with the airtight sealing member 108, the suction unit 101 further comprises the suction pump 601. The suction pump 601 is, for example, an electric suction pump, a mechanical suction pump, etc., that allows a continuous air pumping action in the suction unit 101. In this embodiment, the suction unit 101 is made of an incompressible material such as polystyrene, or a metal such as stainless steel or aluminum. As illustrated in FIG. 1, the tubular connection member 104 is rigidly connected to the suction unit 101 via the intermediate connection member 103 and the annular sealing member 102. The tubular connection member 104 is operably connected to the upper end 106b of the suction chamber 106 and extends towards a lower end 106a of the suction chamber 106 positioned within the suction unit 101. More specifically, the tubular connection member 104 extends substantially towards the lower end 106a of the suction chamber 106 such that the lower end 104b of the tubular connection member 104 is positioned proximal to an airtight sealing member 108 at the lower end 106a of the suction chamber 106. The suction pump 601 is operably connected to the suction chamber 106 via an air line tube 107 in the suction unit 101. The air line tube 107 is positioned proximal to an upper end 106b of the suction chamber 106 and substantially above a lower end 104b of the tubular connection member 104. Moreover, the air line tube 107 projects perpendicular to at least one side (e.g., such as the side 106c of the suction chamber 106 from the suction pump 601) of the suction chamber 106 into the inner space 110 of the suction chamber 106. Further, the projected air line tube 107 protruding out of the at least one side of the suction chamber 106 is positioned substantially perpendicular to the tubular connecting member 104 which is extending towards the lower end 106a of the suction chamber 106. Such a placement of the air line tube 107 and the tubular connecting member 104 precludes any suctioned intraoral biofilm that flows through the tubular connection member 104 from entering the air line tube 107. The electric suction pump 601 comprises an electrical on/off switch 602 and an electrical power supply connection 603. The electrical on/off switch 602 is used to activate or deactivate the suction pump 601. The suction pump 601 is powered through the electrical power supply connection 603 connected to an external power supply (not shown). The suction pump 601 creates a negative air pressure in the inner space 110 of the suction chamber 106 for suctioning the intraoral biofilm from the intraoral areas through the angular head member 105 and via the tubular connection member 104 into the inner space 110 of the suction chamber 106. The suction pump 601 creates a negative air pressure below the standard atmosphere pressure (atm), for example, between about 0.99 atm to about 0.2 atm in the inner space 110 of the suction chamber 106. A user, for example, a dentist can open the lower end 106a of the suction chamber 106 by opening the airtight sealing member 108 to drain the intraoral biofilm accumulated in the suction chamber 106.

FIG. 6B exemplarily illustrates a front elevation view of another embodiment of the embodiment shown in FIG. 6A. The intraoral biofilm control apparatus 100 illustrated in FIG. 6B includes a circular suction plate 901 connected to an upper end 104a of the tubular connection member 104 of the intraoral biofilm control apparatus 100. More specifically, the angular head member 105 of the intraoral biofilm control apparatus 100 comprises the generally circular suction plate 901 in place of the suction tip 105a. The circular suction plate 901 is in fluid communication with the inner space 110 of the suction chamber 106 in the suction unit 101 via the tubular connection member 104. The circular suction plate 901 comprises a front surface 901a and a rear surface 901b (not visible in FIG. 6B). The circular suction plate 901 is configured to suction the intraoral biofilm from intraoral tongue areas into the inner space 110 of the suction chamber 106 when a negative pressure is created in the inner space 110 of the suction chamber 106. Moreover, the front surface 901a of the circular suction plate 901 is configured with multiple projections 901c for scraping the intraoral biofilm from the intraoral tongue areas. It is noted that, the angular head member 105 is shown to be curved for example purposes only and that the angular head member 105 can be of another shape or size to allow the angular head member 105 to access and contact different intraoral areas, for example, tongue areas, areas under the tongue, gum areas, etc. The circular suction plate 901 is explained in more detail in the description of FIGS. 9A, 9B, 10A and 10B.

Figure 7A:
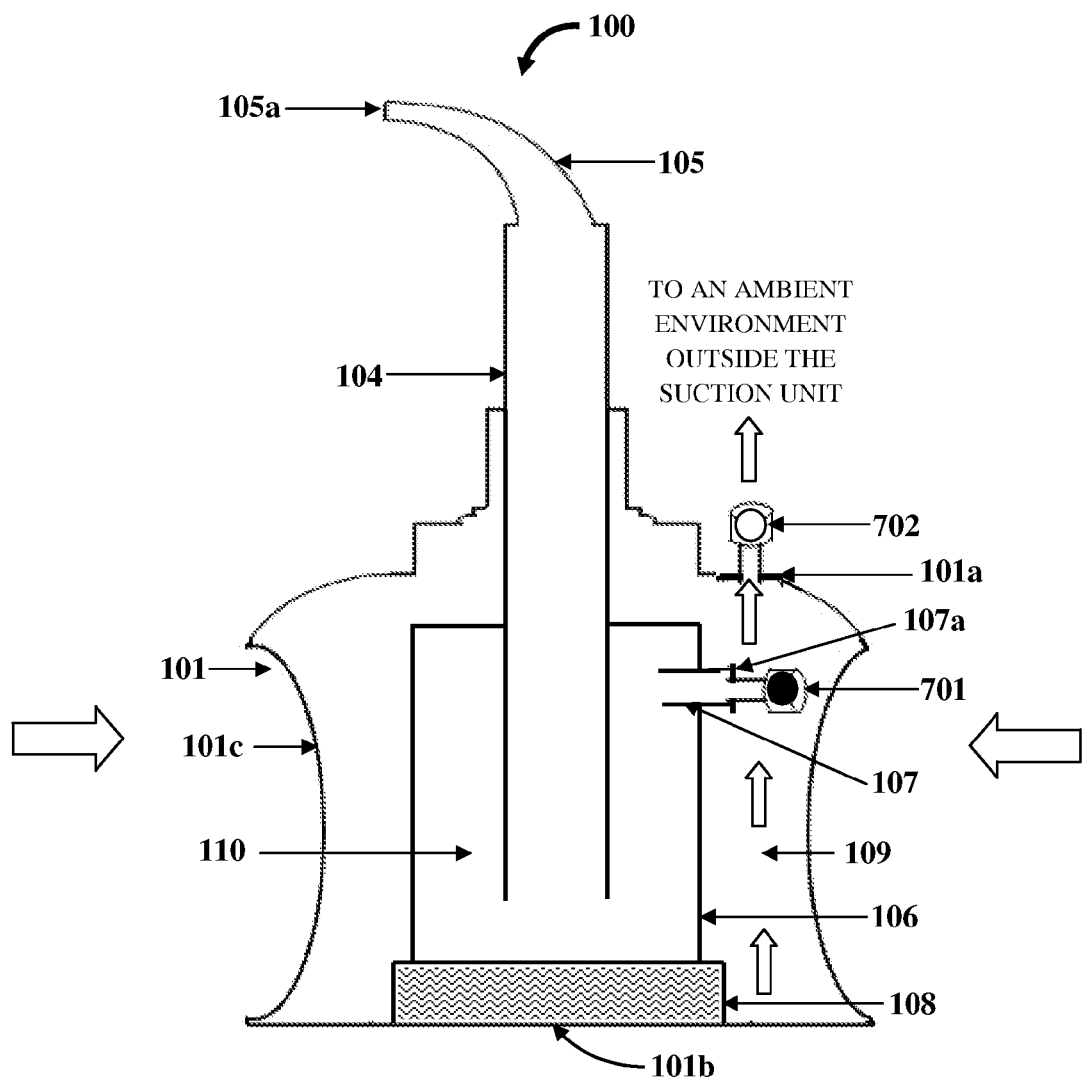
FIGS. 7A-7B exemplarily illustrate sectional views of another embodiment of the intraoral biofilm control apparatus, showing a suction unit when compressed and decompressed respectively.
Figure 7B:
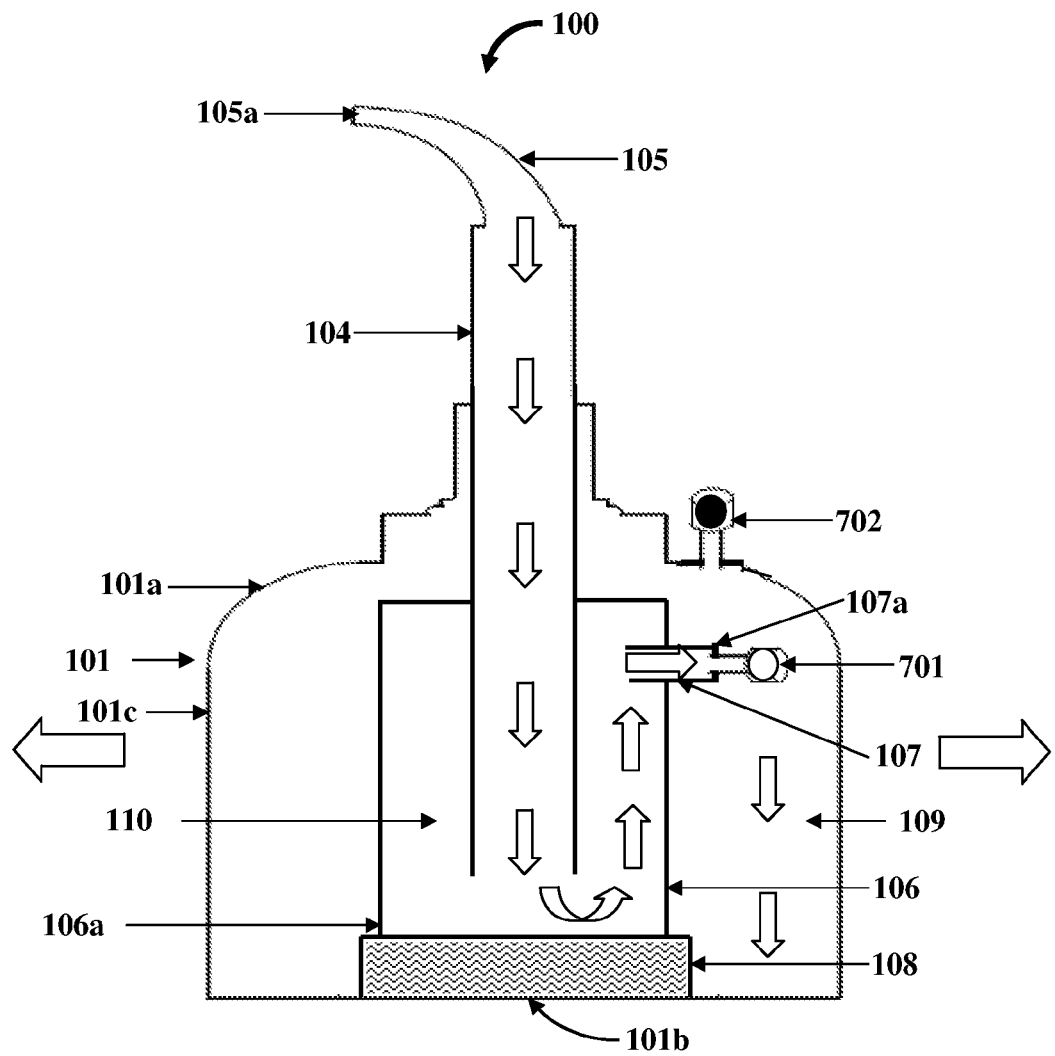

FIGS. 7A-7B exemplarily illustrate sectional views of another embodiment of the intraoral biofilm control apparatus 100, showing a suction unit 101 when compressed and decompressed respectively. In this embodiment, the suction unit 101 comprises the suction chamber 106, the air line tube 107, the airtight sealing member 108, an inflow valve 701, and an outflow valve 702. In this embodiment, the suction unit 101 is configured as a compressible bottle shaped container with a generally cylindrical wall 101c, an upper surface 101a, and a generally circular lower surface 101b, defining an inner space 109 of the suction unit 101. In this embodiment, the outflow valve 702 is operably connected to the suction unit 101, for example, at the upper surface 101a of the suction unit 101. The outflow valve 702, when opened, allows a unidirectional flow of air from the inner space 109 of the suction unit 101 to an ambient environment outside the suction unit 101 for enabling a continuous air pumping action. The inflow valve 701 is operably connected to a distal end 107a of the air line tube 107. The distal end 107a of the air line tube 107 is in fluid communication with the inner space 109 of the suction unit 101. When the suction unit 101 is manually compressed by exerting a moderate amount of pressure on the cylindrical wall 101c of the suction unit 101, as exemplarily illustrated in FIG. 7A, for example, by a user's hand, the inflow valve 701 closes and the outflow valve 702 opens to exhaust air from the inner space 109 of the suction unit 101 to the ambient environment outside the suction unit 101. When the suction unit 101 is decompressed, by removing the compressive pressure from the cylindrical wall 101c of the suction unit 101, the suction unit 101 retracts to an original decompressed configuration of the suction unit 101, as exemplarily illustrated in FIG. 7B, and a negative air pressure is created in the inner space 109 defined within the suction unit 101 as a result of the air exhausted during compression of the suction unit 101. On decompressing the suction unit 101, the outflow valve 702 closes and the inflow valve 701 opens. The open inflow valve 701 and the negative air pressure created allows a unidirectional flow of air from the inner space 110 of the suction chamber 106 into the inner space 109 of the suction unit 101, through the air line tube 107, thereby allowing a continuous air pumping action on compression and decompression of the suction unit 101. The continuous air pumping action as a result of the continuous compression and decompression of the suction unit 101 maintains a negative air pressure inside the suction chamber 106, thereby allowing a continuous suctioning of the intraoral biofilm through the suction tip 105a of the angular head member 105 into the inner space 110 of the suction chamber 106.

Figure 8:
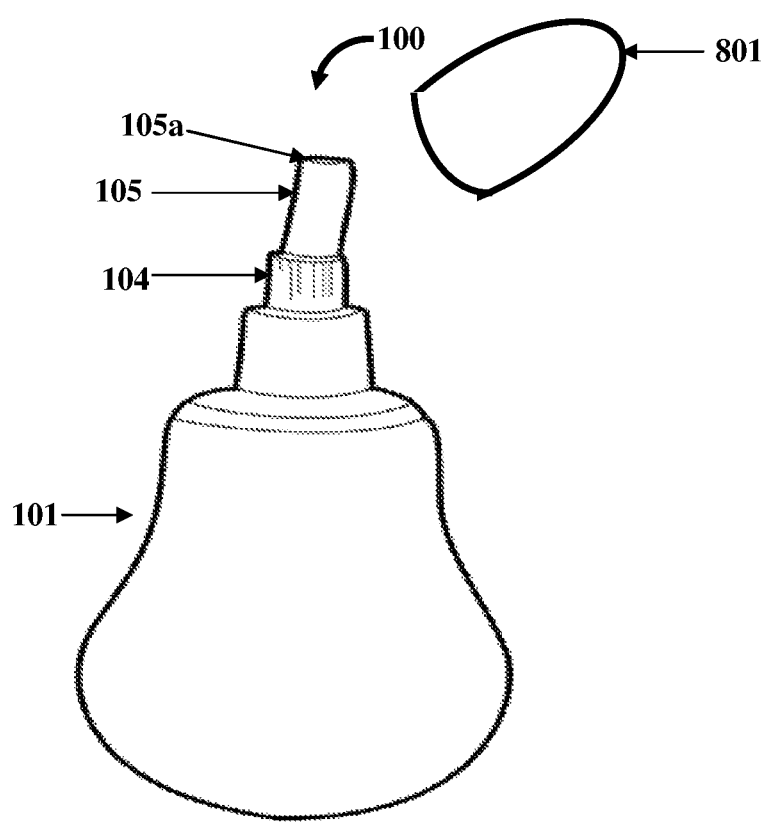
FIG. 8 exemplarily illustrates an embodiment of the intraoral biofilm control apparatus for an infant user.

FIG. 8 exemplarily illustrates an embodiment of the intraoral biofilm control apparatus 100 for an infant user. In this embodiment, the angular head member 105 of the intraoral biofilm control apparatus 100 is made of a soft flexible material to flexibly remove the intraoral biofilm from the intraoral areas of the infant user without hurting the infant user. Infant users who are vulnerable to bacteria from their parents through oral fluid can use this type of the intraoral biofilm control apparatus 100 because their oral cavities are too fragile for cleaning by a toothbrush. The suction tip 105a of the angular head member 105 made of a flexible material mimics the suction action of an infant user for suctioning the intraoral biofilm formed in the oral cavity of the infant user. The suction tip 105a of the angular head member 105 is configured in the shape of a nipple that can tease the erupting teeth and tongue of the infant user. The angular head member 105, in fluid communication with the inner space 110 of the suction chamber 106 (not shown in FIG. 8) positioned within the suction unit 101, via the tubular connection member 104, suctions the intraoral biofilm from the intraoral areas of the infant user, when a negative air pressure is created in the inner space 110 of the suction chamber 106 as disclosed in the detailed description of FIGS. 1A-7B. In an embodiment, a removable cap 801 may be positioned on the angular head member 105 for precluding bacterial contamination of the angular head member 105.

Figure 9A:
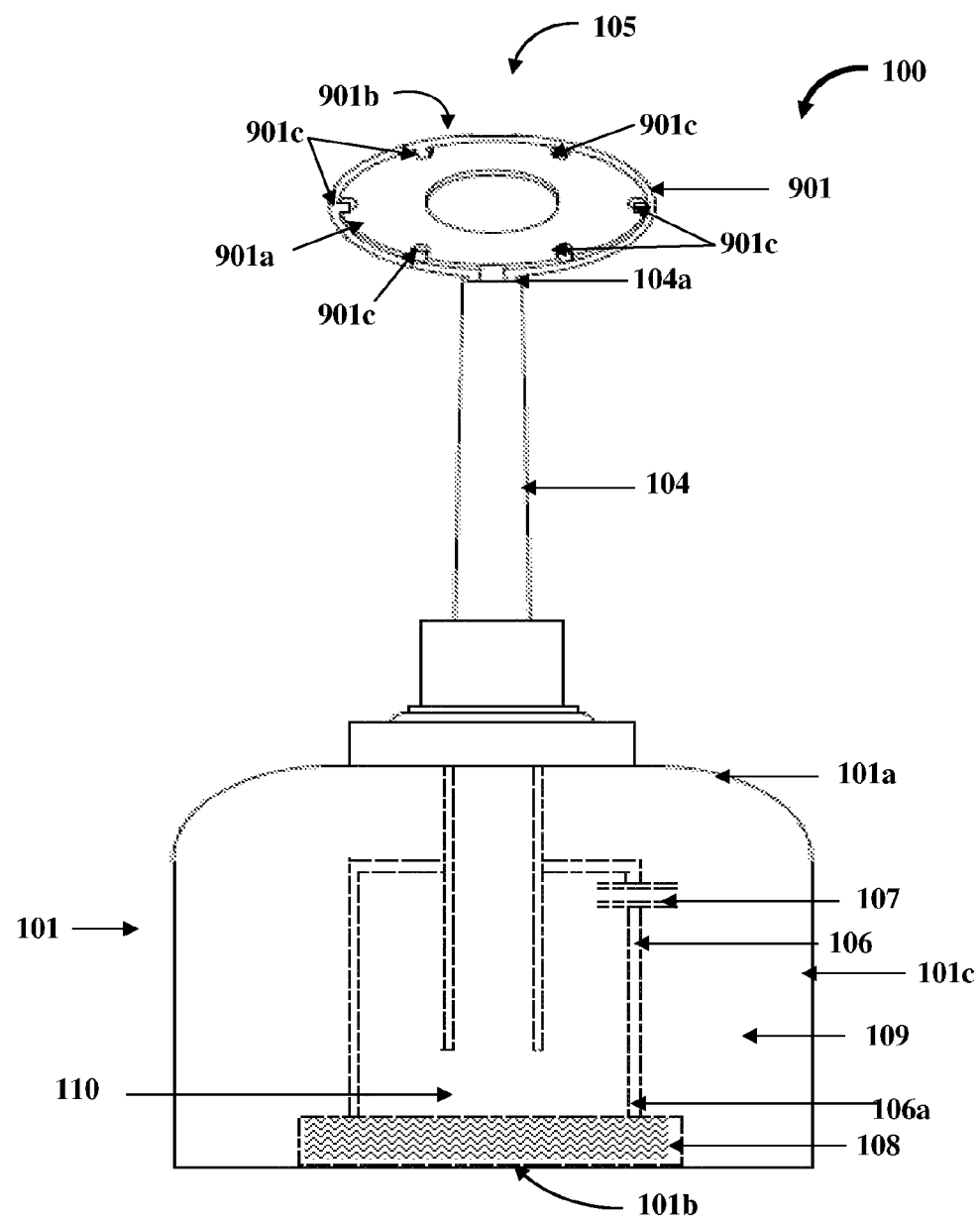
FIG. 9A exemplarily illustrates a front elevation view of another embodiment of the intraoral biofilm control apparatus, showing the suction unit and a circular suction plate connected to an upper end of a tubular connection member of the intraoral biofilm control apparatus.

FIG. 9A exemplarily illustrates a front elevation view of another embodiment of the intraoral biofilm control apparatus 100, showing the suction unit 101 and a circular suction plate 901 connected to the upper end 104a of the tubular connection member 104 of the intraoral biofilm control apparatus 100. The suction unit 101 is configured as a compressible bottle shaped container with a generally cylindrical wall 101c, an upper surface 101a, and a generally circular lower surface 101b, defining an inner space 109 of the suction unit 101. In an embodiment, the angular head member 105 of the intraoral biofilm control apparatus 100 comprises a generally circular suction plate 901 removably connected to the upper end 104a of the tubular connection member 104. The generally circular suction plate 901 is a generally flat plate used for scraping and suctioning a broad area of a tongue surface to suction the intraoral biofilm from the tongue surface. The circular suction plate 901, in fluid communication with the inner space 110 of the suction chamber 106 in the suction unit 101 via the tubular connection member 104, suctions the intraoral biofilm from intraoral tongue areas into the inner space 110 of the suction chamber 106 when a negative air pressure is created in the inner space 110 of the suction chamber 106 as disclosed in the detailed description of FIGS. 4A-4B. A user, for example, a dentist can open the lower end 106a of the suction chamber 106 by opening the airtight sealing member 108 to drain the accumulated intraoral biofilm.

Figure 9B:
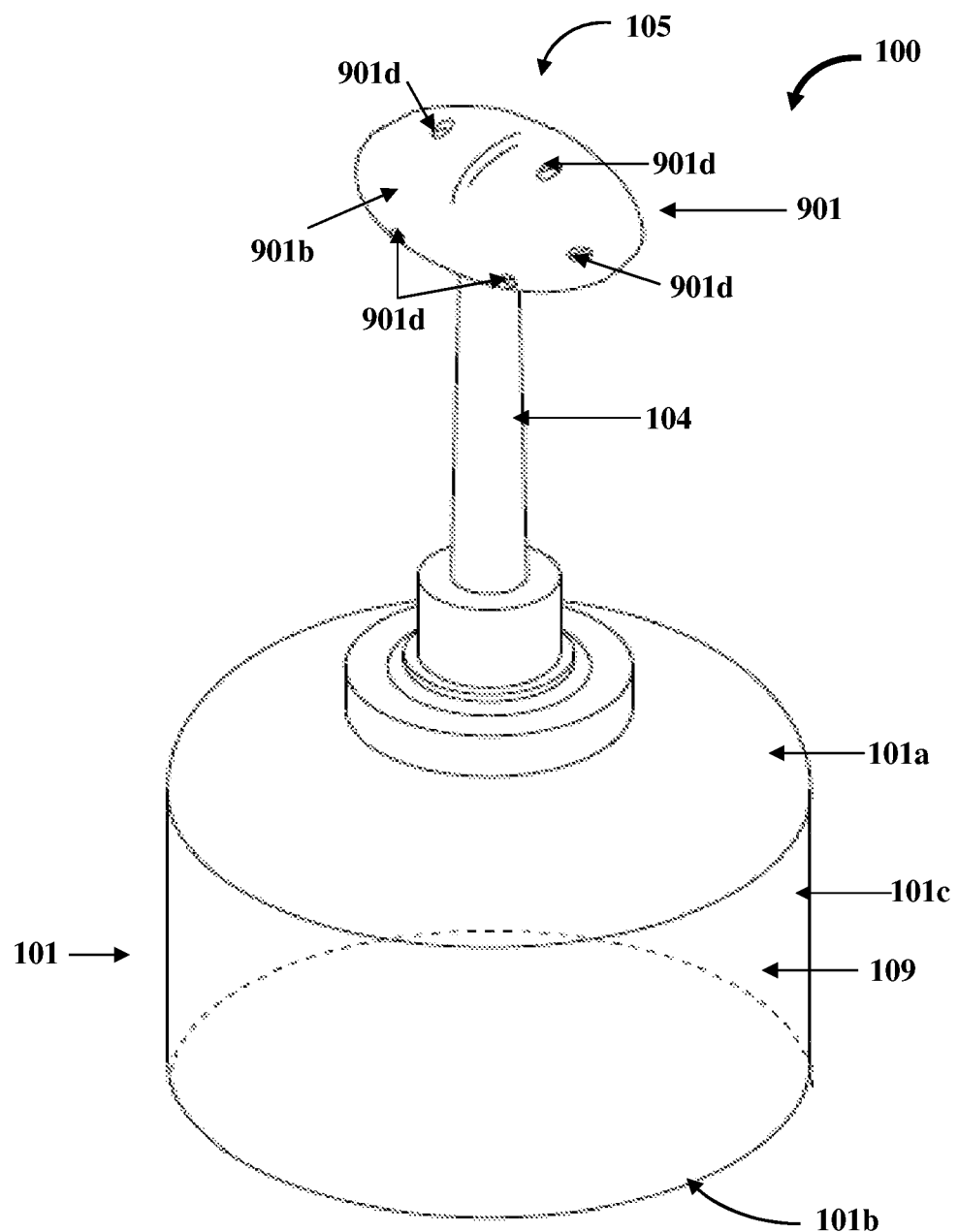
FIG. 9B exemplarily illustrates a rear isometric view of the embodiment of the intraoral biofilm control apparatus shown in FIG. 9A.

The circular suction plate 901 comprises a front surface 901a and a rear surface 901b as exemplarily illustrated in FIGS. 9A-9B. The front surface 901a is configured with multiple projections 901c for scraping the intraoral biofilm from the intraoral tongue areas. When a negative air pressure is created in the inner space 110 of the suction chamber 106, the intraoral biofilm on the intraoral tongue surface is suctioned through the circular suction plate 901 into the inner space 110 of the suction chamber 106 via the tubular connection member 104. In an embodiment, the circular suction plate 901 is connected to the tubular connection member 104 via an elongate member (not shown) that allows an extension of the length of the tubular connection member 104 for accessing inaccessible intraoral tongue areas.

FIG. 9B exemplarily illustrates a rear isometric view of the embodiment of the intraoral biofilm control apparatus 100 shown in FIG. 9A. Not shown in FIG. 9B, in dashed lines, is the suction chamber 106, the air line tube 107, and the airtight sealing member 108 positioned inside the suction unit 101 as exemplarily illustrated in FIG. 9A. In an embodiment, the rear surface 901b of the circular suction plate 901 is configured with multiple openings 901d. In another embodiment, the openings 901d are configured on the front surface 901a of the circular suction plate 901 exemplarily illustrated in FIG. 9A. In another embodiment, the openings 901d are configured on the front surface 901a and the rear surface 901b of the circular suction plate 901. The openings 901d are configured as additional structures through which the intraoral biofilm, for example, plaque and debris is collected and suctioned into the inner space 110 of the suction chamber 106, via the tubular connection member 104 when a negative air pressure is created in the inner space 110 of the suction chamber 106. The openings 901d of the circular suction plate 901 are configured to remove the intraoral biofilm as soon as the intraoral biofilm is disrupted and mobilized within saliva fluid.

Figure 10A:
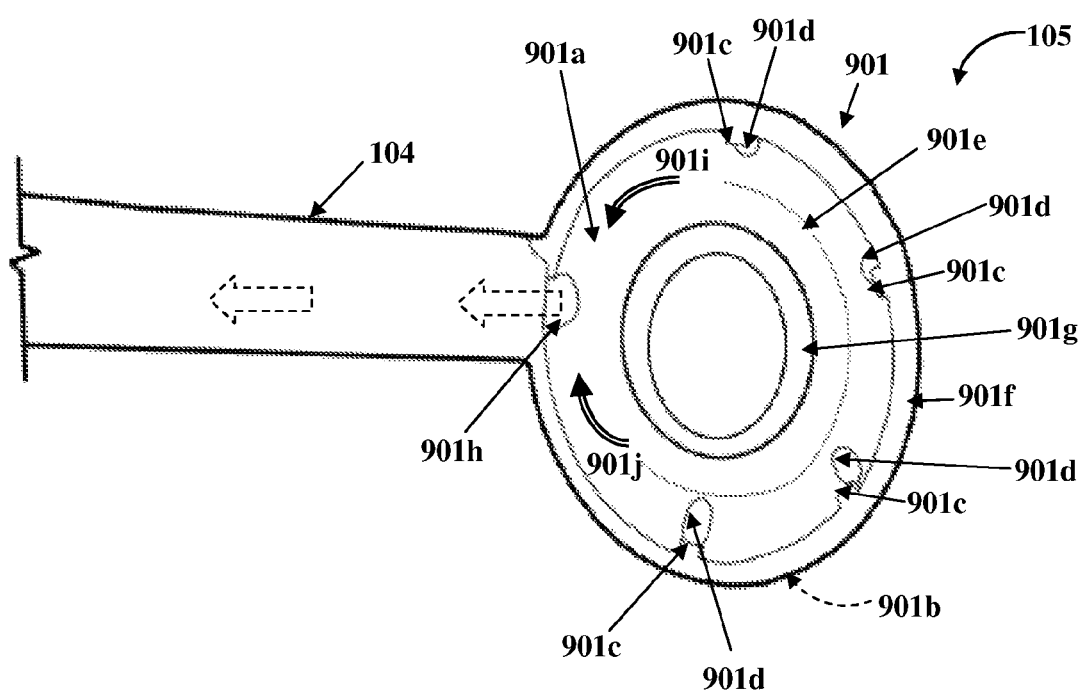
FIGS. 10A-10B exemplarily illustrate enlarged perspective views of the circular suction plate connected to the tubular connection member of the embodiment of the intraoral biofilm control apparatus shown in FIGS. 9A-9B.
Figure 10B:
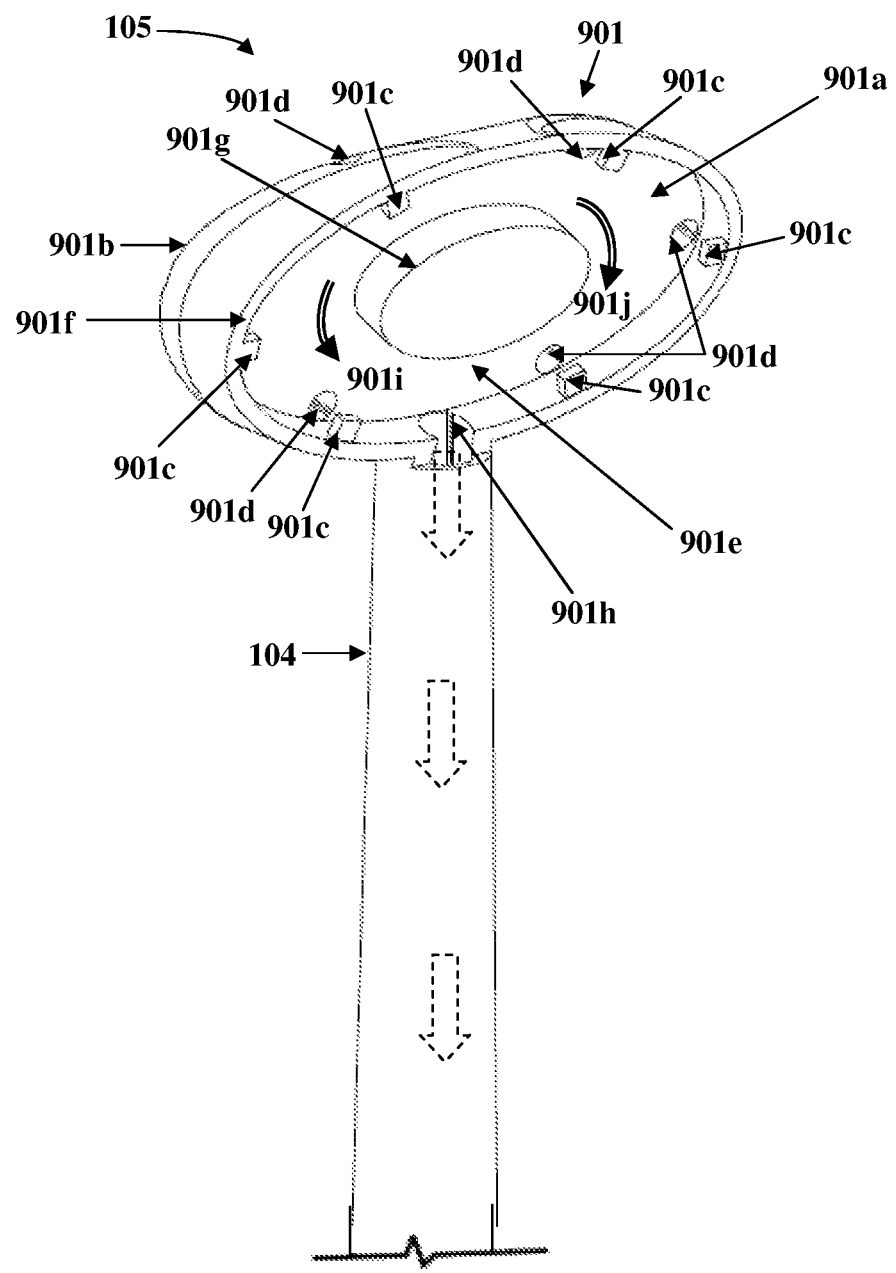

FIGS. 10A-10B exemplarily illustrate enlarged perspective views of the circular suction plate 901 connected to the tubular connection member 104 of the embodiment of the intraoral biofilm control apparatus 100 shown in FIGS. 9A-9B. When a user, for example, a dentist positions the front surface 901a of the circular suction plate 901 on an intraoral tongue area, the projections 901c configured on the front surface 901a of the circular suction plate 901 can be used to scrape the intraoral biofilm from the intraoral tongue area. The intraoral biofilm present on the intraoral tongue area can be scraped, disrupted, and displaced onto intraoral tongue areas and intraoral areas, proximal to the intraoral tongue area that is in contact with the front surface 901a of the circular suction plate 901. The scraping of the intraoral biofilm from the intraoral tongue area can be performed when the suction unit 101 exemplarily illustrated in FIGS. 9A-9B, is in a compressed configuration.

In an embodiment, on scraping the intraoral biofilm, the disrupted and displaced intraoral biofilm is suctioned from the intraoral tongue areas into an annular space 901e defined between an outer peripheral surface 901f and an inner peripheral surface 901g of the circular suction plate 901 via the openings 901d, due to a negative air pressure created in the suction chamber 106 exemplarily illustrated in FIG. 9A. In this embodiment, the intraoral biofilm is suctioned from the annular space 901e in flow directions 901i and 901j to a groove 901h in fluid communication with the tubular connection member 104, and thereafter into the inner space 110 of the suction chamber 106 via the tubular connection member 104 in the direction indicated by arrows in FIGS. 10A-10B. In another embodiment, when the circular suction plate 901 is inserted under the tongue and the floor of the mouth or between the tongue and a side of the gingival wall, the openings 901d configured on the front surface 901a and the rear surface 901b of the circular suction plate 901 suction the disrupted and displaced intraoral biofilm from the intraoral tongue areas and other intraoral areas and transfer the disrupted and displaced intraoral biofilm to the tubular connection member 104 via the groove 901h and then into the inner space 110 of the suction chamber 106 in the direction indicated by arrows in FIGS. 10A-10B.

Decompression of the suction unit 101 exemplarily illustrated in FIGS. 9A-9B, creates a negative air pressure in the suction chamber 106 in the suction unit 101 as disclosed in the detailed description of FIG. 4A. Due to the negative air pressure created, the intraoral biofilm accumulated in the annular space 901e of the circular suction plate 901 is suctioned through the groove 901h into the tubular connection member 104 and then into the inner space 110 of the suction chamber 106 from the tubular connection member 104.

Figures 11A, 11B:
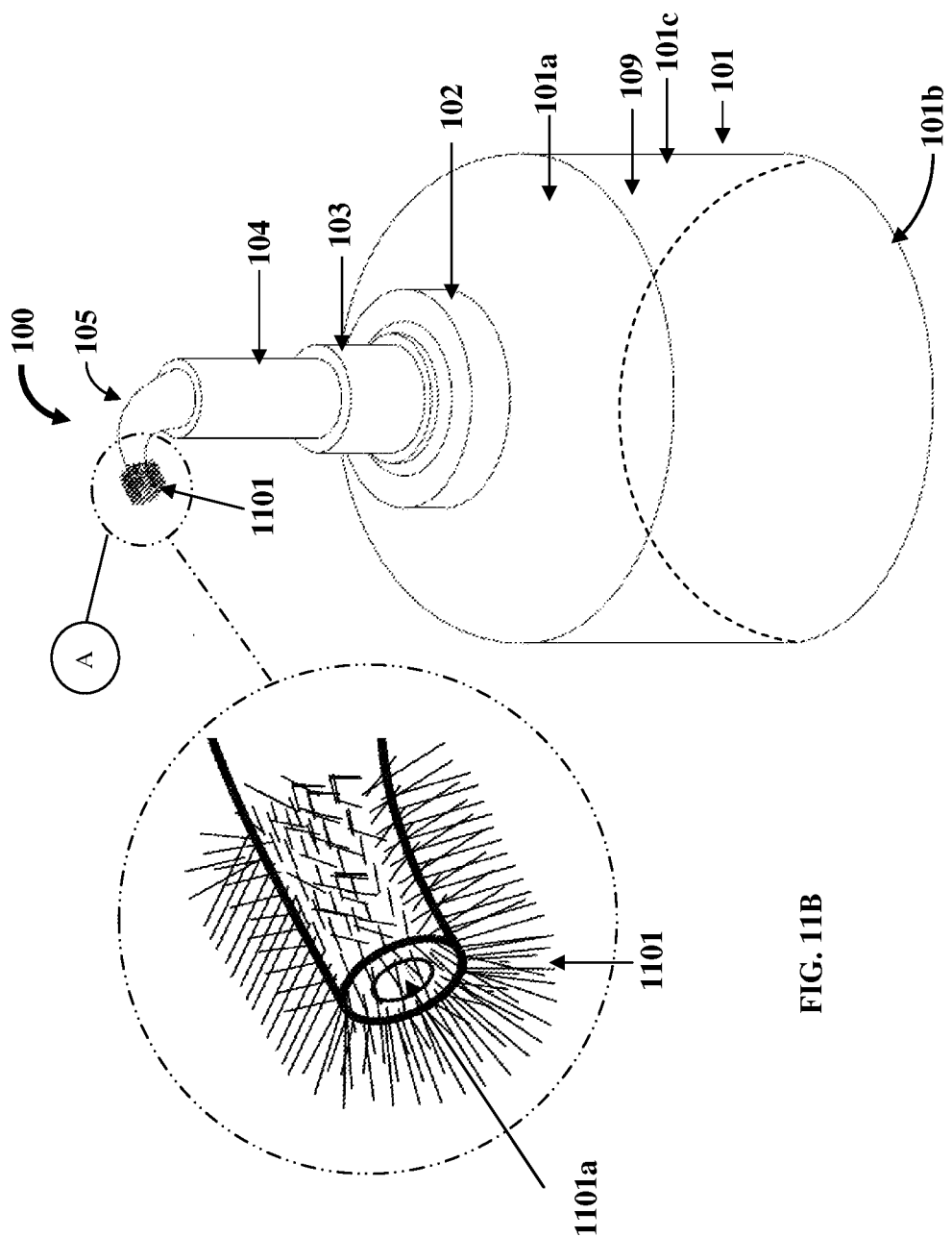
FIG. 11A exemplarily illustrates a top perspective view of another embodiment of the intraoral biofilm control apparatus, showing a micro brush tip positioned on an upper end of the angular head member of the intraoral biofilm control apparatus.
FIG. 11B exemplarily illustrates an enlarged view of a portion of the intraoral biofilm control apparatus marked "A" in FIG. 11A, showing the micro brush tip.
Figure 11C:
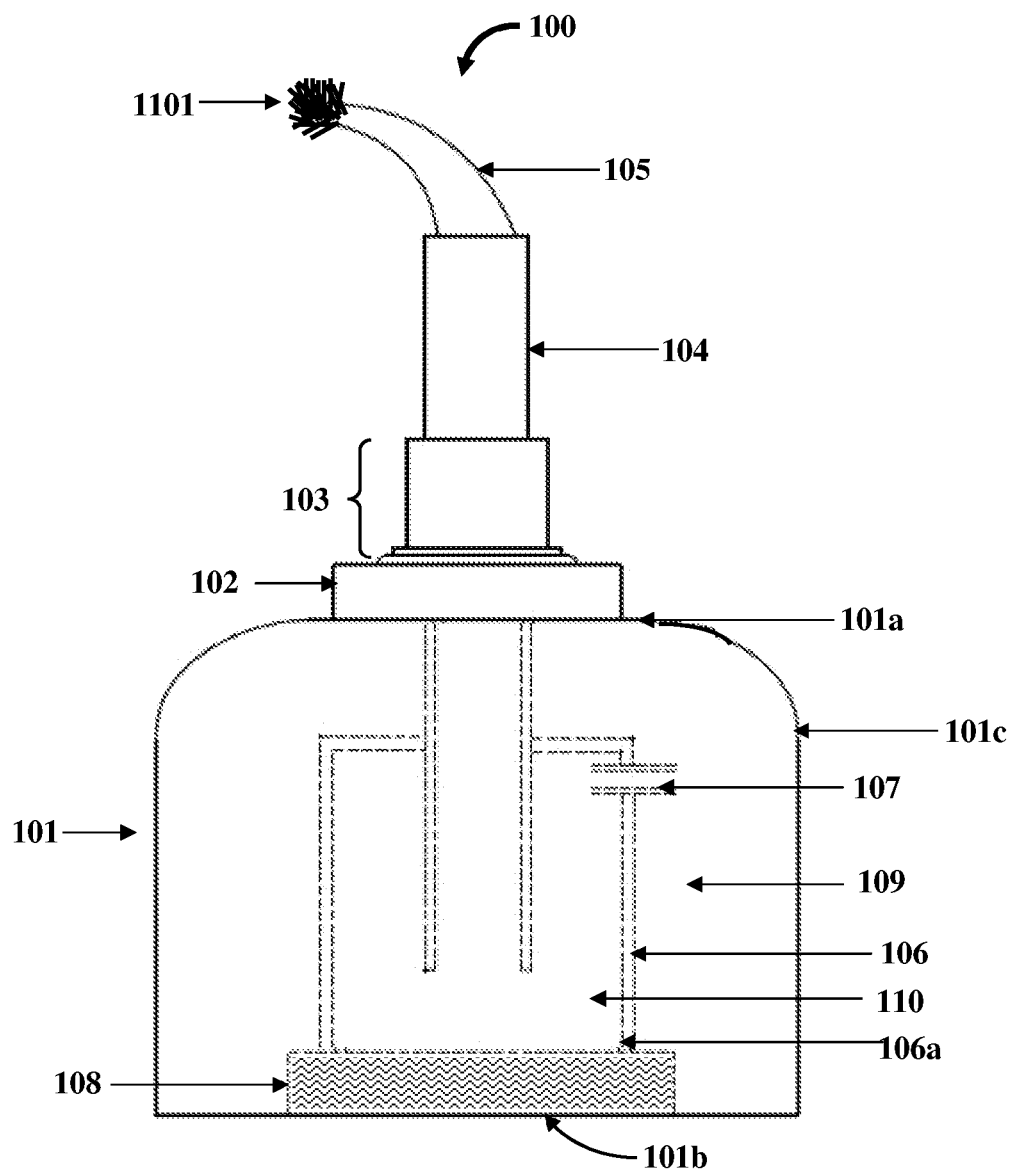
FIG. 11C exemplarily illustrates a front elevation view of the embodiment of the intraoral biofilm control apparatus shown in FIG. 11A.

FIG. 11A exemplarily illustrates a top perspective view of another embodiment of the intraoral biofilm control apparatus 100, showing a micro brush tip 1101 positioned on an upper end 105c of the angular head member 105 of the intraoral biofilm control apparatus 100. Not shown in FIG. 11A, in dashed lines, is the suction chamber 106, the air line tube 107, and the airtight sealing member 108 positioned inside the suction unit 101 as exemplarily illustrated in FIG. 11C. The intraoral biofilm control apparatus 100 comprises the suction unit 101 configured as a compressible bottle shaped container with a generally cylindrical wall 101c, an upper surface 101a, and a generally circular lower surface 101b that define an inner space 109 of the suction unit 101. In this embodiment, the angular head member 105 comprises the micro brush tip 1101 positioned on the upper end 105c of the angular head member 105. FIG. 11B exemplarily illustrates an enlarged view of a portion of the intraoral biofilm control apparatus 100 marked "A" in FIG. 11A, showing the micro brush tip 1101. The micro brush tip 1101 is configured to remove the intraoral biofilm from readily accessible intraoral areas. FIG. 11C exemplarily illustrates a front elevation view of the embodiment of the intraoral biofilm control apparatus 100 shown in FIG. 11A. In this embodiment, the micro brush tip 1101 can be used for disrupting the intraoral biofilm from readily accessible intraoral areas, for example, areas in between artificial prosthesis such as braces, dental partials, etc. In an embodiment, the intraoral biofilm disrupted by the micro brush tip 1101 is suctioned through an opening 1101a configured in the micro brush tip 1101. When a negative air pressure in the inner space 110 of the suction chamber 106 of the intraoral biofilm control apparatus 100, the disrupted intraoral biofilm is suctioned through the opening 1101a in the micro brush tip 1101, into the tubular connection member 104, and thereafter into the inner space 110 of the suction chamber 106. A user, for example, a dentist can then open the lower end 106a of the suction chamber 106 by opening the airtight sealing member 108 to drain the accumulated intraoral biofilm.

Figure 12A:
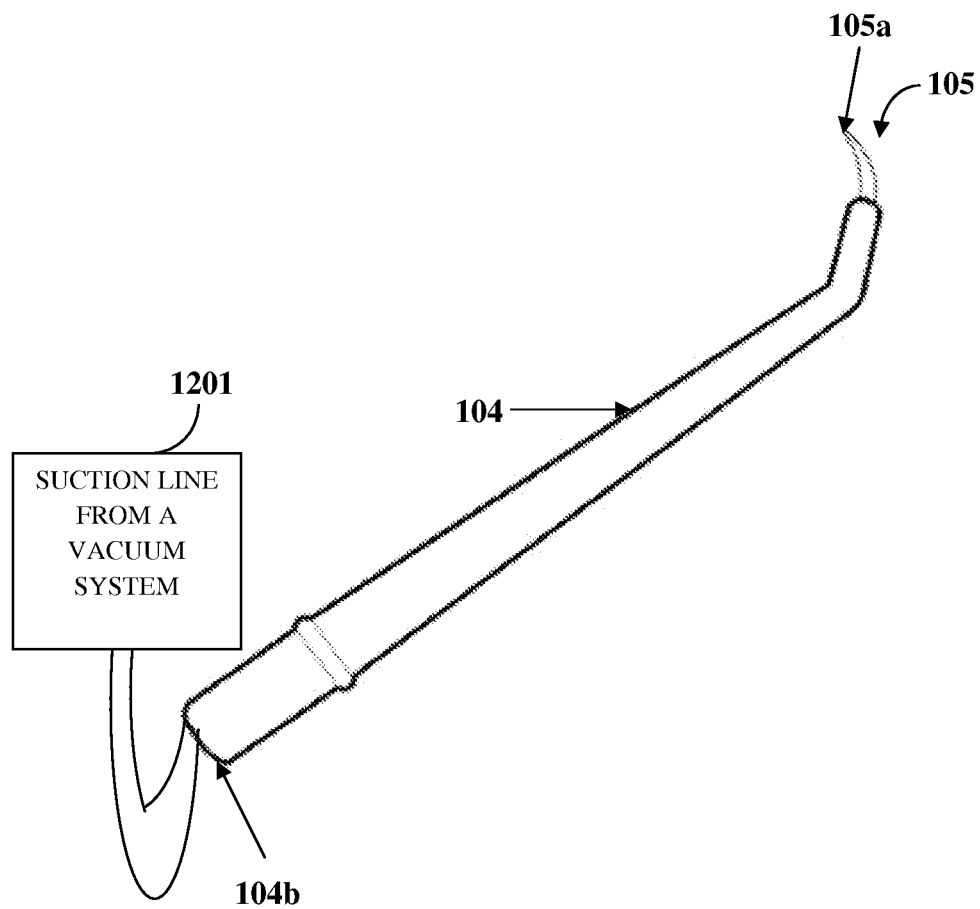
FIGS. 12A-12B exemplarily illustrate perspective views of another embodiment of the intraoral biofilm control apparatus, showing the angular head member of the intraoral biofilm control apparatus configured for a direct connection to a suction line.
Figure 12B:
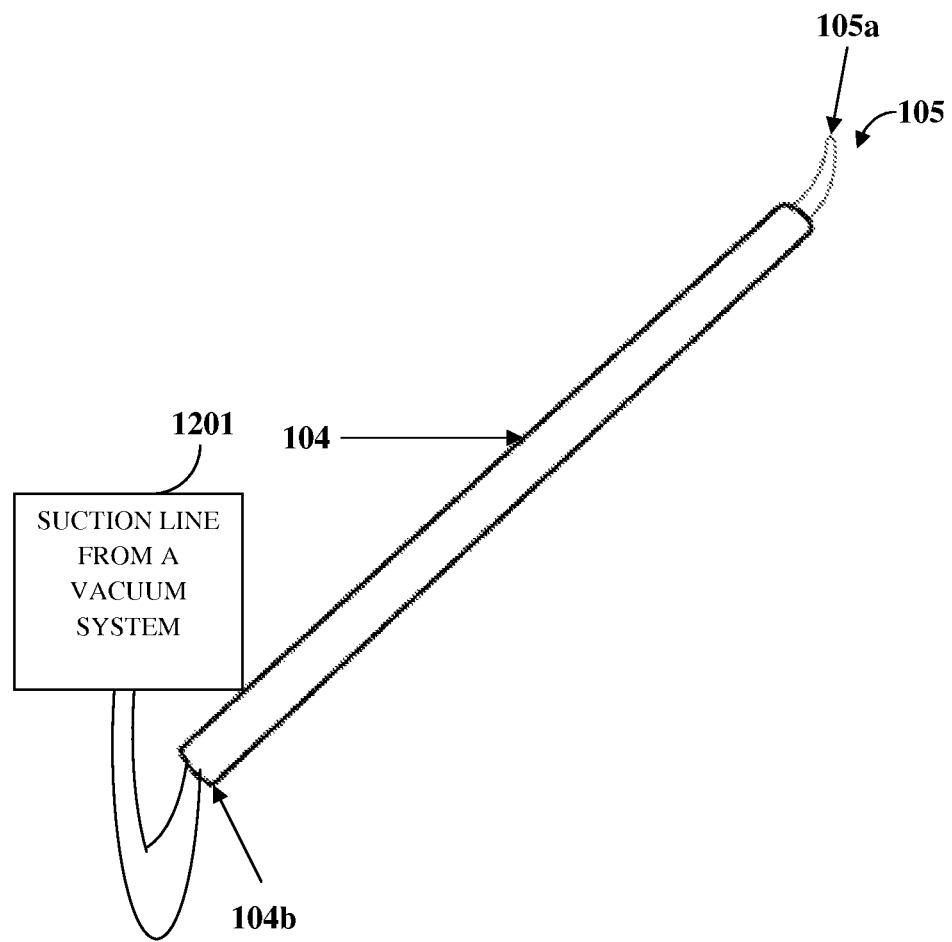

FIGS. 12A-12B exemplarily illustrate perspective views of another embodiment of the intraoral biofilm control apparatus 100 exemplarily illustrated in FIGS. 1A-1B, showing the angular head member 105 of the intraoral biofilm control apparatus 100 configured for a direct connection to a suction line 1201. In this embodiment, the suction unit 101 is a suction line 1201, for example, a dental suction line connected to a vacuum system or a vacuum source used in a dental office. The suction line 1201 is operably connected to the lower end 104b of the tubular connection member 104. The suction line 1201 is a line drawn from one or more dental or medical vacuum systems that can create a negative air pressure for suctioning the intraoral biofilm from the intraoral areas in contact with the angular head member 105, through the tubular connection member 104. An example of a dental vacuum system is a dental suction pump. The suction line 1201 produces a preset vacuum pressure, for example, preset to a negative pressure of between about 0.99 atmosphere pressure (atm) to about 0.2 atm to suction the intraoral biofilm from the intraoral areas. The tubular connection member 104 that connects to the suction line 1201 may be angled as exemplarily illustrated in FIG. 12A, or linear as exemplarily illustrated in FIG. 12B. The suction tip 105a of the angular head member 105 can also be used for suctioning the intraoral biofilm, for example, from a periodontal pocket when a patient is receiving a periodontal treatment, etc. The suction tip 105a can replace use of dental equipment, for example, an aspirating needle used in an endodontic treatment. The suction tip 105a can be used for different dental examinations, for example, to detect a direct cavity that is sensitive to the negative air pressure. In another embodiment, the suction tip 105a is configured as a disposable suction tip to preclude oral cross contamination among patients.

Figure 13:
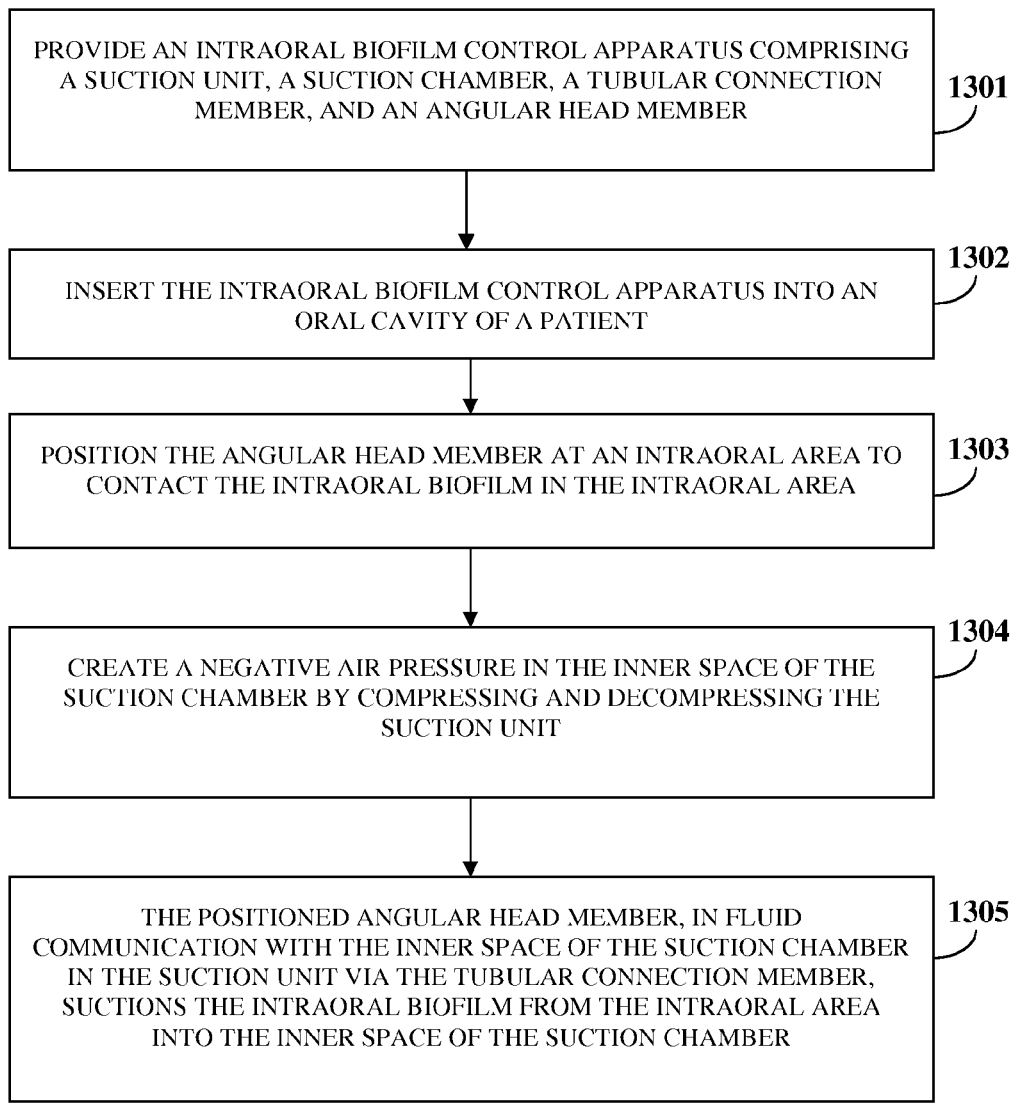
FIG. 13 illustrates a method for suctioning an intraoral biofilm from intraoral areas.

FIG. 13 illustrates a method for suctioning an intraoral biofilm from intraoral areas. In the method disclosed herein, the intraoral biofilm control apparatus 100 comprising the suction unit 101, the suction chamber 106, the tubular connection member 104, and the angular head member 105 as exemplarily illustrated in FIG. 1A, is provided 1301. The intraoral biofilm control apparatus 100 is inserted 1302 into an oral cavity of the patient, that is, into the patient's mouth. The angular head member 105 of the inserted intraoral biofilm control apparatus 100 is positioned 1303 by a user, for example, a dentist to contact the intraoral biofilm in the intraoral area. A negative air pressure is created 1304 in the inner space 110 of the suction chamber 106 of the inserted intraoral biofilm control apparatus 100 by compressing and decompressing the suction unit 101 of the inserted intraoral biofilm control apparatus 100, as disclosed in different embodiments of the intraoral biofilm control apparatus 100 in the detailed descriptions of FIGS. 4A-7B. When the negative air pressure is created in the inner space 110 of the suction chamber 106, the positioned angular head member 105, in fluid communication with the inner space 110 of the suction chamber 106 in the suction unit 101 via the tubular connection member 104, suctions 1305 the intraoral biofilm from the intraoral area into the inner space 110 of the suction chamber 106. The suctioned intraoral biofilm from the intraoral area is accumulated into the suction chamber 106. The accumulated intraoral biofilm is drained from the suction chamber 106 by opening the airtight sealing member 108 connected to the lower end 106a of the suction chamber 106.

The different embodiments of the intraoral biofilm control apparatus 100 disclosed in the detailed descriptions of FIGS. 1A-12B, allow access between the teeth, prostheses, and tongue surface, and remove the disrupted intraoral biofilm directly from the oral cavity, thereby precluding swallowing or relocating of bacteria in the oral cavity. The intraoral biofilm control apparatus 100 disclosed herein may be used after brushing and flossing teeth. After using the intraoral biofilm control apparatus 100 disclosed herein, oral rinsing agents, for example, biotene may be used to replenish saliva lost during suctioning. In a dental office, the intraoral biofilm control apparatus 100 disclosed herein can be used after a dental prophylaxis (prophy) appointment to remove prophy paste residues between teeth surfaces.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention in its aspects.

We claim:

1. An intraoral biofilm control apparatus comprising:
   a suction unit configured as a flexible container defining an inner space;
   a suction chamber positioned within and in communication with said inner space of said suction unit, said suction chamber configured to receive an intraoral biofilm suctioned from intraoral areas into an inner space defined within said suction chamber;
   a suction pump operably connected to said suction chamber via an air line tube in said suction unit, said suction pump configured to create a negative air pressure in said inner space of said suction chamber for suctioning said intraoral biofilm from said intraoral areas into said inner space of said suction chamber;
   a tubular connection member operably connected to said suction unit and extending substantially towards a lower end of said suction chamber, wherein a lower end of the tubular connection member is positioned proximal to an airtight sealing member at the lower end of the suction chamber within said suction unit, wherein said tubular connection member is in fluid communication with said inner space of said suction chamber;
   said air line tube positioned proximal to an upper end of the suction chamber and substantially above the lower end of the tubular connection member, wherein said air line tube projects perpendicular to at least one side of said suction chamber from said suction pump into said inner space of said suction chamber, and wherein said air line tube protrudes substantially perpendicular to said tubular connecting member; and
   an angular head member adjustably connected to an upper end of said tubular connection member, said angular head member configured to contact said intraoral biofilm in said intraoral areas, wherein said angular head member, in fluid communication with said inner space of said suction chamber in said suction unit via said tubular connection member, is further configured to suction said intraoral biofilm from said intraoral areas into said inner space of said suction chamber when said negative air pressure is created in said inner space of said suction chamber.

2. The intraoral biofilm control apparatus of claim 1, wherein said angular head member comprises a suction tip positioned on an upper end of said angular head member, wherein said angular head member is rotatably connected to said tubular connection member to enable said suction tip to configurably access said intraoral areas and contact said intraoral biofilm in said intraoral areas.

3. The intraoral biofilm control apparatus of claim 2, wherein said suction tip is angularly curved to reach inaccessible said intraoral areas.

4. The intraoral biofilm control apparatus of claim 2, wherein said suction tip is removably connected to said upper end of said angular head member for enabling replacement of said suction tip.

5. The intraoral biofilm control apparatus of claim 1, wherein said airtight sealing member at said lower end of said suction chamber is configured to open said lower end of said suction chamber for draining said received intraoral biofilm from said suction chamber.

6. The intraoral biofilm control apparatus of claim 1, wherein said angular head member is made of a flexible material configured to flexibly remove said intraoral biofilm from said intraoral areas.

7. The intraoral biofilm control apparatus of claim 1, wherein said angular head member comprises a micro brush tip positioned on an upper end of said angular head member, wherein said micro brush tip is configured to remove said intraoral biofilm from readily accessible said intraoral areas.

8. The intraoral biofilm control apparatus of claim 1, wherein said angular head member comprises a generally circular suction plate removably connected to said upper end of said tubular connection member, wherein said generally circular suction plate, in fluid communication with said inner space of said suction chamber in said suction unit via said tubular connection member, is configured to suction said intraoral biofilm from intraoral tongue areas into said inner space of said suction chamber when said negative air pressure is created in said inner space of said suction chamber.

9. An intraoral biofilm control apparatus comprising:
a suction unit configured as a container defining an inner space;
a suction chamber positioned within and in communication with said inner space of said suction unit, said suction chamber configured to receive an intraoral biofilm suctioned from intraoral areas into an inner space defined within said suction chamber;
a suction pump operably connected to said suction chamber via an air line tube in said suction unit, said suction pump configured to create a negative air pressure in said inner space of said suction chamber for suctioning said intraoral biofilm from said intraoral areas into said inner space of said suction chamber;
a tubular connection member operably connected to said suction unit and extending substantially towards a lower end of said suction chamber, wherein a lower end of the tubular connection member is positioned proximal to an airtight sealing member at the lower end of the suction chamber within said suction unit, wherein said tubular connection member is in fluid communication with said inner space of said suction chamber;
said air line tube positioned proximal to an upper end of the suction chamber and substantially above the lower end of the tubular connection member, wherein said air line tube projects perpendicular to at least one side of said suction chamber from said suction pump into said inner space of said suction chamber, and wherein said air line tube protrudes substantially perpendicular to said tubular connecting member; and
an angular head member adjustably connected to an upper end of said tubular connection member, said angular head member configured to contact said intraoral biofilm in said intraoral areas, wherein said angular head member, in fluid communication with said inner space of said suction chamber in said suction unit via said tubular connection member, is further configured to suction said intraoral biofilm from said intraoral areas into said inner space of said suction chamber when said negative air pressure is created in said inner space of said suction chamber.

* * * * *